US006139832A

United States Patent [19]
Li et al.

[11] Patent Number: 6,139,832
[45] Date of Patent: Oct. 31, 2000

[54] LEUKOCYTE ADHESION INHIBITOR-1 (LAI-1) POLYPEPTIDES

[75] Inventors: Haodong Li, Gaithersburg; Brent L. Kreider, Germantown, both of Md.

[73] Assignee: Human Genome Sciences, Inc., Rockville, Md.

[21] Appl. No.: 08/943,336

[22] Filed: Oct. 3, 1997

Related U.S. Application Data

[63] Continuation-in-part of application No. 08/724,871, Oct. 4, 1996, abandoned, which is a continuation-in-part of application No. PCT/US96/09572, Jun. 5, 1996, and a continuation-in-part of application No. 08/464,401, Jun. 5, 1995, abandoned, and a continuation-in-part of application No. 08/460,987, Jun. 5, 1995, abandoned, and a continuation-in-part of application No. PCT/US95/01780, Feb. 8, 1995

[60] Provisional application No. 60/027,769, Oct. 4, 1996.

[51] Int. Cl.⁷ ......................... A61K 38/19; C07K 14/52; C12N 15/19

[52] U.S. Cl. ...................... 424/85.1; 435/69.5; 435/71.1; 435/71.2; 435/252.3; 435/320.1; 435/325; 435/471; 530/351; 930/140; 536/23.5

[58] Field of Search ..................................... 530/350, 351; 930/140; 435/69.5, 71.1, 71.2, 252.3, 320.1, 325, 471; 536/23.1, 23.5; 424/85.1

[56] References Cited

U.S. PATENT DOCUMENTS

| | | | |
|---|---|---|---|
| 4,897,348 | 1/1990 | Johnson et al. | 435/69.1 |
| 5,278,287 | 1/1994 | Rollins et al. | 530/351 |
| 5,306,709 | 4/1994 | Gewirtz | 514/12 |
| 5,346,686 | 9/1994 | Lyle et al. | 424/1.41 |
| 5,605,817 | 2/1997 | Coleman et al. | 435/69.5 |
| 5,633,149 | 5/1997 | Guegler et al. | 435/69.5 |

FOREIGN PATENT DOCUMENTS

| | | |
|---|---|---|
| 0 488 900 | 6/1992 | European Pat. Off. . |
| WO 91/04274 | 4/1991 | WIPO . |
| WO 94/12537 | 6/1994 | WIPO . |
| WO 96/17868 | 6/1996 | WIPO . |
| WO 96/22374 | 7/1996 | WIPO . |
| WO 96/24668 | 8/1996 | WIPO . |
| WO 96/39522 | 12/1996 | WIPO . |
| WO 97/15594 | 5/1997 | WIPO . |
| WO 98/11226 | 3/1998 | WIPO . |

OTHER PUBLICATIONS

Bowie et al, Science vol. 247, pp. 1306–1310, 1990.

George et al. Macromolecular Sequencing & Synthesis, vol. 12, pp. 127–149, Alan R. Liss, Inc. New York, 1988.

Colditz, I., et al., "In Vivo Inflammatory Activity of Neutrophil–Activating Factor, a Novel Chemotactic Peptide Derived from Human Monocytes," *Am. J. Pathology* 134:755–760 (1989).

Bischoff, S.C. et al., "Monocyte Chemotactic Protein 1 is a Potent Activator of Human Basophils," *J. Exp. Med.* 175:1271–1275 (May 1992).

Blum, S. et al., "Three Human Homologs of a Murine Gene Encoding an Inhibitor of Stem Cell Proliferation," *DNA and Cell Biol.* 9(8):589–602 (1990).

Brown, K.D. et al., "A Family of Small Inducible Proteins Secreted by Leukocytes Are members of a New Superfamily that Includes Leukocyte and Fibroblast–Derived Inflammatory Agents, Growth Factors, and Indicators of Various Activation Processes," *J. Immunol.* 142(2):679–687 (Jan. 1989).

Cunningham, B.C. and J.A. Wells, "High–resolution epitope mapping of hGH–receptor interactions by alanine–scanning mutagenesis," *Science* 244:1080–1085 (1989).

Derynck, R. et al., "Recombinant Expression, Biochemical Characterization, and Biological Activities of the Human MGSA/gro Protein," *Biochem.* 29:10225–10233 (1990).

Goodman, R.B. et al., "Molecular Cloning of Porcine Alveolar Macrophage–Derived Neutrophil Chemotactic Factors I and II: Identification of Porcine Il–8 and Another Intercrine–α Protein," *Biochem.* 31(43):10483–10490 (1992).

Harlow, E. and D. Lane, *Antibodies: a laboratory manual*, Cold Spring Spring harbor Laboratory, Cold Spring Harbor, NY; p. 76 (1988).

Jose, P.J. et al., "Ectaxin: A Potent Eosinophil Chemoattractant Cytokine Detected in a Guinea Pig Model of Allergic Airways Inflammation," *J. Exp. Med.* 179:881–887 (Mar. 1994).

Kuna, P. et al., "Moncyte Chemotactic and Activating Factor is a Potent Histamine–releasing Factor for Human Basophils," *J. Exp. Med.* 175:489–493 (Feb. 1992).

Kurdowska, A. et al., "Biological and Kinetic Characterization of Recombinant Human Macrophage Inflammatory Peptides 2 Alpha and Beta and Comparison With the Neutrophil Activating Peptide 2 and Interleukin 8," *Cytokine* 6(2):124–134 (Mar. 1994).

Kwon, B.S. and S.M. Weissman, "cDNA sequences of two inducible T–cell genes," *Proc. Natl. Acad. Sci. USA* 86:1963–1967 (Mar. 1989).

Lukacs, N.W. et al., "The Role of Macrophage Inflammatory Protein 1α in *Schistosoma mansoni* Egg–induced Granulomatous Inflammation," *J. Exp. Med.* 177:1551–1559 (Jun. 1993).

Matsushima, K. et al., "Purification and Characterization of a Novel Monocyte Chemotactic and Activating Factor Produced By a Human Myelomonocytic Cell Line," *J. Exp. Med.* 169:1485–1490 (Apr. 1989).

Nakao, M. et al., "Structures of Human Genes Coding for Cytokine LD78 and Their Expression," *Mol. Cell. Biol.* 10(7):3646–3658 (Jul. 1990).

(List continued on next page.)

*Primary Examiner*—Prema Mertz
*Attorney, Agent, or Firm*—Sterne, Kessler, Goldstein & Fox P.L.L.C.

[57] ABSTRACT

There are disclosed therapeutic compositions and methods using isolated nucleic acid molecules encoding a human chemokine beta-11 (Ck beta-11) polypeptide and a human leukocyte adhesion inhibitor-1 (LAI-1) polypeptide (previously termed chemokine α1(CKα1 or ckα-1), as well as Ck beta-11 and/or LAI-1 polypeptides themselves, as are vectors, host cells and recombinant methods for producing the same.

14 Claims, 11 Drawing Sheets

OTHER PUBLICATIONS

Obaru, K. et al., "A cDNA Clone Used to Study mRNA Inducible in Human Tonsillar Lymphocytes by a Tumor Promoter," *J. Biochem.* 99:885–894 (1986).

Schall, T.J., "Biology of the Rantes/Sis Cytokine Family," *Cytokine 3(3)*:165–183 (May 1991).

Sudo, K. et al., "2058 Expressed Sequence Tags (ESTs) from a Human Fetal Lung cDNA Library," *Genomics* 24:276–279 (Dec. 1994).

Zipfel, P.F. et al., "Mitogenic Activation of Human T Cells Induces Two Closely Related Genes Which Share Structural Similarities With a New Family of Secreted Factors," *J. Imunol. 142(5)*:1582–1590 (Mar. 1989).

English Language Abstract of EP 0 488 900 (Document AM1), WPI Acc No: 92–185765/23.

International Search Report for Appl. No. PCT/US 97/17716, mailed Feb. 1998.

ATGGCCCTGCTACTGGCCCTCAGCCTGCTGGTTCTCTGGACTTCCCCAGCCCCAACTCTG
M   A   L   L   L   A   L   S   L   L   V   L   W   T   S   P   A   P   T   L

AGTGGCACCAATGATGCTGAAGACTGCTGCCTGTCTGTGACCCAGAAACCCATCCCTGGG
S   G   T   N   D   A   E   D   C   C   L   S   V   T   Q   K   P   I   P   G

TACATCGTGAGGAACTTCCACTACCTTCTCATCAAGGATGGTTGCAGGGTGCCTGCTGTA
Y   I   V   R   N   F   H   Y   L   L   I   K   D   G   C   R   V   P   A   V

GTGTTCACCACACTGAGGGGCCGCCAGCTCTGTGCACCCCAGACCAGCCCTGGGTAGAA
V   F   T   T   L   R   G   R   Q   L   C   A   P   P   D   Q   P   W   V   E

CGCATCATCCAGAGACTGCAGAGGACCTCAGCCAAGATGAAGCGCCGCAGCAGTTAA
R   I   I   Q   R   L   Q   R   T   S   A   K   M   K   R   R   S   S   *

FIG. 1

```
ATGAAGTTCATCTCGACATCTCTGCTTCTCATGCTGCTGGTCAGCAGCCTCTCTCCAGTC
 M  K  F  I  S  T  S  L  L  M  L  L  V  S  S  L  S  P  V

CAAGGTGTTCTGGAGGTCTATTACACAAGCTTGAGGTGTAGATGTGTCCAAGAGAGCTCA
 Q  G  V  L  E  V  Y  Y  T  S  L  R  C  R  C  V  Q  E  S  S

GTCTTTATCCCTAGACGCTTCATTGATCGAATTCAAATCTTGCCCCGTGGGAATGGTTGT
 V  F  I  P  R  R  F  I  D  R  I  Q  I  L  P  R  G  N  G  C

CCAAGAAAAGAAATCATAGTCTGGAAGAAGAACAAGTCAATTGTGTGTGTGGACCCTCAA
 P  R  K  E  I  I  V  W  K  K  N  K  S  I  V  C  V  D  P  Q

GCTGAATGGATACAAAGAATGATGGAAGTATTGAGAAAAAGAAGTTCTTCAACTCTACCA
 A  E  W  I  Q  R  M  M  E  V  L  R  K  R  S  S  S  T  L  P

GTTCCAGTGTTTAAGAGAAAGATTCCCTGA
 V  P  V  F  K  R  K  I  P  *
```

FIG.2

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..294

(xi) SEQUENCE DESCRIPTION: SEQ ID NO:1:

```
ATG GCC CTG CTA CTG GCC CTC AGC CTG CTG GTT CTC TGG ACT TCC CCA        48
Met Ala Leu Leu Leu Ala Leu Ser Leu Leu Val Leu Trp Thr Ser Pro
 1               5                  10                  15

GCC CCA ACT CTG AGT GGC ACC AAT GAT GCT GAA GAC TGC TGC CTG TCT        96
Ala Pro Thr Leu Ser Gly Thr Asn Asp Ala Glu Asp Cys Cys Leu Ser
             20                  25                  30

GTG ACC CAG AAA CCC ATC CCT GGG TAC ATC GTG AGG AAC TTC CAC TAC       144
Val Thr Gln Lys Pro Ile Pro Gly Tyr Ile Val Arg Asn Phe His Tyr
         35                  40                  45

CTT CTC ATC AAG GAT GGT TGC AGG GTG CCT GCT GTA GTG TTC ACC ACA       192
Leu Leu Ile Lys Asp Gly Cys Arg Val Pro Ala Val Val Phe Thr Thr
     50                  55                  60

CTG AGG GGC CGC CAG CTC TGT GCA CCC CCA GAC CAG CCC TGG GTA GAA       240
Leu Arg Gly Arg Gln Leu Cys Ala Pro Pro Asp Gln Pro Trp Val Glu
 65                  70                  75                  80

CGC ATC ATC CAG AGA CTG CAG AGG ACC TCA GCC AAG ATG AAG CGC CGC       288
Arg Ile Ile Gln Arg Leu Gln Arg Thr Ser Ala Lys Met Lys Arg Arg
                 85                  90                  95

AGC AGT TAA                                                            297
Ser Ser
```

(2) INFORMATION FOR SEQ ID NO:2:

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Leu Leu Leu Ala Leu Ser Leu Leu Val Leu Trp Thr Ser Pro
 1               5                  10                  15
```

```
Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser (2) INFORMATION FOR SEQ ID NO:3:

(i) SEQUENCE CHARACTERISTICS:
        (A) LENGTH: 330 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..327

(xi) SEQUENCE DESCRIPTION: SEQ ID NO:3:

ATG AAG TTC ATC TCG ACA TCT CTG CTT CTC ATG CTG CTG GTC AGC AGC        48
Met Lys Phe Ile Ser Thr Ser Leu Leu Leu Met Leu Leu Val Ser Ser
 1               5                  10                  15

CTC TCT CCA GTC CAA GGT GTT CTG GAG GTC TAT TAC ACA AGC TTG AGG        96
Leu Ser Pro Val Gln Gly Val Leu Glu Val Tyr Tyr Thr Ser Leu Arg
            20                  25                  30

TGT AGA TGT GTC CAA GAG AGC TCA GTC TTT ATC CCT AGA CGC TTC ATT       144
Cys Arg Cys Val Gln Glu Ser Ser Val Phe Ile Pro Arg Arg Phe Ile
        35                  40                  45

GAT CGA ATT CAA ATC TTG CCC CGT GGG AAT GGT TGT CCA AGA AAA GAA       192
Asp Arg Ile Gln Ile Leu Pro Arg Gly Asn Gly Cys Pro Arg Lys Glu
    50                  55                  60

ATC ATA GTC TGG AAG AAG AAC AAG TCA ATT GTG TGT GTG GAC CCT CAA       240
Ile Ile Val Trp Lys Lys Asn Lys Ser Ile Val Cys Val Asp Pro Gln
65                  70                  75                  80

GCT GAA TGG ATA CAA AGA ATG ATG GAA GTA TTG AGA AAA AGA AGT TCT       288
Ala Glu Trp Ile Gln Arg Met Met Glu Val Leu Arg Lys Arg Ser Ser
                85                  90                  95

TCA ACT CTA CCA GTT CCA GTG TTT AAG AGA AAG ATT CCC TGA               330
Ser Thr Leu Pro Val Pro Val Phe Lys Arg Lys Ile Pro
                100                 105

(2) INFORMATION FOR SEQ ID NO:4:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Phe Ile Ser Thr Ser Leu Leu Leu Met Leu Leu Val Ser Ser
 1               5                  10                  15

Leu Ser Pro Val Gln Gly Val Leu Glu Val Tyr Tyr Thr Ser Leu Arg
            20                  25                  30
```

```
Cys Arg Cys Val Gln Glu Ser Ser Val Phe Ile Pro Arg Arg Phe Ile
        35                  40                  45

Asp Arg Ile Gln Ile Leu Pro Arg Gly Asn Gly Cys Pro Arg Lys Glu
    50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

CCCGCATGCC AACTCTGAGT GGCACCA                                      27

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

CCCGGATCCC AATGCTTCGG ACT                                          23

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

CCCGCATGCC TTCTGGAGGT CTATTACACA                                   30

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

CCCGGATCCG GGAATCTTTC TCTTAAAC                                     28
```

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

```
AAAAAGCTTG CCATGGCCCT GCTACTG                                27
```

(2) INFORMATION FOR SEQ ID NO:10:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

```
CGCTCTAGAT TAAGCGTAGT CTGGGACGTC GTATGGGTAT AGGTTAACTG CTGCGAC    57
```

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

```
AAAAAGCTTA GAATGAAGTT CATCTCG                                27
```

(2) INFORMATION FOR SEQ ID NO:12:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

```
CGCTCTAGAT TAAGCGTAGT CTGGGACGTC GTATGGGTAG GGAATCTTTC TCTT    54
```

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

```
CGCGGGATCC GCCATCATGG CCCTGCTACT GGCCCT                          36
```

-continued (2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

CGGCGGTACC TGGCTGCACG GTCCATAGG          29

(2) INFORMATION FOR SEQ ID NO:15:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:15:

GCCGGATCCG CCATCATGAA GTTCATCTCG ACATC          35

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:16:

CGCGGGTACC GGTGTTCTTA GTGGAAA          27

LEUKOCYTE ADHESION INHIBITOR-1 (LAI-1) POLYPEPTIDES

CROSS REFERENCE TO RELATED APPLICATIONS

This application claims the benefit of the filing date of provisional application Ser. No. 60/027,769 filed Oct. 4, 1996, which is herein incorporated by reference; this application is also a continuation-in-part of application Ser. No. 08/724,871 filed Oct. 4, 1996, now abandoned, which is herein incorporated by reference; said application Ser. No. 08/724,871 is a continuation-in-part of each of the following applications: PCT/US96/09572, filed in the U.S. Receiving Office on Jun. 5, 1996, Ser. No. 08/464,401 filed on Jun. 5, 1995, now abandoned, and Ser. No. 08/460,987 filed on Jun. 5, 1995, now abandoned; said application numbers PCT/US96/09572, Ser. No. 08/464,401, and Ser. No. 08/460,987 are each continuations-in-part of application number PCT/US95/01780 filed in the United States Receiving Office on Feb. 8, 1995.

BACKGROUND OF THE INVENTION

1. Field of the Invention

The present invention relates to novel chemokine polypeptides and encoding nucleic acids. More specifically, therapeutic compositions and methods are provided using isolated nucleic acid molecules encoding a human chemokine beta-11 (Ck beta-11) polypeptide; and a human leukocyte adhesion inhibitor (LAI-1) polypeptide (previously termed chemokine α1(CKα1 or cka-1)), as well as Ck beta-11 and/or LAI-1 polypeptides themselves, as are vectors, host cells and recombinant methods for producing the same.

2. Related Art

Chemokines, also referred to as intercrine cytokines, are a subfamily of structurally and functionally related cytokines. These molecules are 8–10 kd in size. In general, chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the "C—X—C" subfamily. In the beta subfamily, the two cysteines are in an adjacent position and are, therefore, referred to as the "C—C" subfamily. Thus far, at least eight different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein 1 (MIP-1) is able to suppress hematopoietic stem cell proliferation, platelet factor-4 (PF-4) is a potent inhibitor of endothelial cell growth, Interleukin-3 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis.

Members of the "C—C" branch exert their effects on the following cells: eosinophils which destroy parasites to lessen parasitic infection and cause chronic inflammation in the airways of the respiratory system; macrophages which suppress tumor formation in vertebrates; and basophils which release histamine which plays a role in allergic inflammation. However, members of one branch can exert an effect on cells which are normally responsive to the other branch of chemokines and, therefore, no precise role can be attached to the members of the branches.

While members of the C—C branch act predominantly on mononuclear cells and members of the C—X—C branch act predominantly on neutrophils a distinct chemoattractant property cannot be assigned to a chemokine based on this guideline.

Some chemokines from one family show characteristics of the other.

SUMMARY OF THE INVENTION

In accordance with one aspect of the present invention, there are provided novel full length or mature polypeptides which are LAI-1 and/or Ck beta-11, as well as biologically active, diagnostically useful or therapeutically useful fragments, analogs and derivatives thereof. LAI-1 and/or Ck beta-11 polypeptides or encoding nucleic acids of the present invention are preferably of animal origin, and more preferably of human origin.

In accordance with another aspect of the present invention there are provided nucleic acid probes comprising nucleic acid molecules of sufficient length to specifically hybridize to Ckβ-11 and LAI-1 sequences.

In accordance with another aspect of the present invention, there are provided polynucleotides (DNA or RNA) which encode such polypeptides and isolated nucleic acid molecules encoding such polypeptides, including mRNAs, DNAs, cDNAs, genomic DNA as well as biologically active and diagnostically or therapeutically useful fragments, analogs and derivatives thereof.

Ck beta-11 Polynucleotides. The present invention also provides isolated nucleic acid molecules comprising a polynucleotide encoding the Ck beta-11 polypeptide having the amino acid sequence shown in FIG. 1 (SEQ ID NO:2) or the amino acid sequence encoded by the cDNA clone deposited in a bacterial host as ATCC Deposit Number 75948 on Nov. 11, 1994. The nucleotide sequence determined by sequencing the deposited Ck beta-11 clone, which is shown in FIG. 1 (SEQ ID NO:1), contains an open reading frame encoding a polypeptide of 98 amino acid residues, with a leader sequence of about 17 amino acid residues, and a predicted molecular weight for the mature protein of about 10 kDa in non-glycosylated form, and about 10–14 kDa in glycosylated form, depending on the extent of glycoslyation. The amino acid sequence of the mature Ck beta-11 protein is shown in FIG. 1, as amino acid residues 18–98 of SEQ ID NO:2.

Thus, one aspect of the invention provides an isolated nucleic acid molecule comprising a polynucleotide having a nucleotide sequence selected from the group consisting of: (1)(a) a nucleotide sequence encoding an Ck beta-11 polypeptide having the complete amino acid sequence in FIG. 1 (SEQ ID NO:2); (1)(b) a nucleotide sequence encoding the mature Ck beta-11 polypeptide having the amino acid sequence at positions 18–98 in FIG. 1 (SEQ ID NO:2); (1)(c) a nucleotide sequence encoding the Ck beta-11 polypeptide having the complete amino acid sequence encoded by the cDNA clone contained in ATCC Deposit No. 75948; (1)(d) a nucleotide sequence encoding the mature Ck beta-11 polypeptide having the amino acid sequence encoded by the cDNA clone contained in ATCC Deposit No. 75948; and (1)(e) a nucleotide sequence complementary to any of the nucleotide sequences in (1)-(a), (b), (c) or (d) above.

LAI-1 Polynucleotides. In one aspect, the present invention provides isolated nucleic acid molecules comprising a polynucleotide encoding the LAI-1 polypeptide having the amino acid sequence shown in FIG. 2 (SEQ ID NO:4) or the amino acid sequence encoded by the cDNA clone deposited in a bacterial host as ATCC Deposit Number 75947 on Nov. 11, 1994. The nucleotide sequence determined by sequencing the deposited LAI-1 clone, which is shown in FIG. 2 (SEQ ID NO:3), contains an open reading frame encoding a polypeptide of 109 amino acid residues, with a leader sequence of about 22 amino acid residues, and a predicted molecular weight of about 110 kDa in non-glycosylated form, and about 11–14 kDa in glycosylated form, depending on the extent of glycoslyation. The amino acid sequence of the mature LAI-1 protein is shown in FIG. 2, as amino acid residues 23–109 of SEQ ID NO:4.

Thus, one aspect of the invention provides an isolated nucleic acid molecule comprising a polynucleotide having a nucleotide sequence selected from the group consisting of: (2)(a) a nucleotide sequence encoding the LAI-1 polypeptide having the complete amino acid sequence in FIG. 2 (SEQ ID NO:4); (2)(b) a nucleotide sequence encoding the mature LAI-1 polypeptide having the amino acid sequence at positions 23–109 in FIG. 2 (SEQ ID NO:4); (2)(c) a nucleotide sequence encoding the LAI-1 polypeptide having the complete amino acid sequence encoded by the cDNA clone contained in ATCC Deposit No. 75947; (2)(d) a nucleotide sequence encoding the mature LAI-1 polypeptide having the amino acid sequence encoded by the cDNA clone contained in ATCC Deposit No.75947; and (2)(e) a nucleotide sequence complementary to any of the nucleotide sequences in (2)-(a), (b), (c) or (d) above.

Ck beta-11 and LAI-1 Polynucleotide Variants. The present invention further relates to variants of the hereinabove described polynucleotides which encode for fragments, analogs and derivatives of the polypeptide having the deduced amino acid sequence of FIGS. 1 and 2 (SEQ ID NOS:2 and 4) or the polypeptides encoded by the cDNA of the deposited clone(s). The variants of the polynucleotides can be a naturally occurring allelic variant of the polynucleotides or a non-naturally occurring variant of the polynucleotides.

Homologous Ck beta-11 and LAI-1 Polynucleotides. Further embodiments of the invention include isolated nucleic acid molecules that comprise a polynucleotide having a nucleotide sequence at least 90% homologous or identical, and more preferably at least 95%, 96%, 97%, 98% or 99% identical, to any of the nucleotide sequences in (1)-, (2)- or (3)-(a), (b), (c), (d) or (e), above, or a polynucleotide which hybridizes under stringent hybridization conditions to a polynucleotide in (1)- or (2)-(a), (b), (c), (d) or (e), above. These polynucleotides which hybridize do not hybridize under stringent hybridization conditions to a polynucleotide having a nucleotide sequence consisting of only A residues or of only T residues.

Nucleic Acid Probes. In accordance with yet another aspect of the present invention, there are also provided nucleic acid probes comprising nucleic acid molecules of sufficient length to specifically hybridize to the Ck beta-11 and/or LAI-1 nucleic acid sequences.

Recombinant Vectors, Host Cells and Expression. The present invention also relates to recombinant vectors, which include the isolated nucleic acid molecules of the present invention, and to host cells containing the recombinant vectors, as well as to methods of making such vectors and host cells and for using them for production of Ck beta-11 and/or LAI-1 polypeptides or peptides by recombinant techniques.

Ck beta-11 Polypeptides. The invention further provides an isolated Ck beta-11 polypeptide having an amino acid sequence selected from the group consisting of: (I)(a) the amino acid sequence of the Ck beta-11 polypeptide having the complete 98 amino acid sequence, including the leader sequence shown in FIG. 1 (SEQ ID NO:2); (I)(b) the amino acid sequence of the mature Ck beta-11 polypeptide (without the leader) having the amino acid sequence at positions 18–98 in FIG. 1 (SEQ ID NO:2); (I)(c) the amino acid sequence of the Ck beta-11 polypeptide having the complete amino acid sequence, including the leader, encoded by the cDNA clone contained in ATCC Deposit No. 75948; and (I)(d) the amino acid sequence of the mature Ck beta-11 polypeptide having the amino acid sequence encoded by the cDNA clone contained in ATCC Deposit No.75948.

LAI-11 Polypeptides. The invention further provides an isolated LAI-1 polypeptide having an amino acid sequence selected from the group consisting of: (II)(a) the amino acid sequence of the LAI-1 polypeptide having the complete 109 amino acid sequence, including the leader sequence shown in FIG. 2 (SEQ ID NO:4); (II)(b) the amino acid sequence of the mature LAI-1 polypeptide (without the leader) having the amino acid sequence at positions 23–109 in FIG. 2 (SEQ ID NO:4); (II)(c) the amino acid sequence of the LAI-1 polypeptide having the complete amino acid sequence, including the leader, encoded by the cDNA clone contained in ATCC Deposit No. 75947; and (II)(d) the amino acid sequence of the mature LAI-1 polypeptide having the amino acid sequence encoded by the cDNA clone contained in ATCC Deposit No. 75947.

Homologous Ck beta-11 and/or LAI-1 Polypeptides. Polypeptides of the present invention also include homologous polypeptides having an amino acid sequence with at least 90% identity, and more preferably at least 95% identity to those described in (I)- and (II)-(a), (b), (c) or (d) above, as well as polypeptides having an amino acid sequence at least 80% identical, more preferably at least 90% identical, and still more preferably 95%, 96%, 97%, 98% or 99% identical to those above.

Ck beta-11 and/or LAI-1 Epitope Bearing Polypeptides and Encoding Polynucleotides. An additional embodiment of this aspect of the invention relates to a peptide or polypeptide which has the amino acid sequence of an epitope-bearing portion of an Ck beta-11 and/or LAI-1 polypeptide having an amino acid sequence described in (I)- or (II)-(a), (b), (c) or (d), above. Peptides or polypeptides having the amino acid sequence of an epitope-bearing portion of an Ck beta-11 and/or LAI-1 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

An additional nucleic acid embodiment of the invention relates to an isolated nucleic acid molecule comprising a polynucleotide which encodes the amino acid sequence of an epitope-bearing portion of an Ck beta-11and/or LAI-1 polypeptide having an amino acid sequence in (I)- or (II)-(a), (b), (c) or (d), above.

Ck beta-11 and/or LAI-1 Antibodies. In accordance with yet a further aspect of the present invention, there is provided an antibody against such polypeptides. In another embodiment, the invention provides an isolated antibody that binds specifically to an Ck beta-11 and/or LAI-1 polypeptide having an amino acid sequence described in (I)- and/or (II)-(a), (b), (c) or (d) above.

The invention further provides methods for isolating antibodies that bind specifically to an Ck beta-11 and/or LAI-1 polypeptide having an amino acid sequence as described herein. Such antibodies are useful diagnostically or therapeutically as described below.

Ck beta-11 and/or LAI-1 Polypeptides, Agonists, Antagonists and Methods. In accordance with yet another aspect of the present invention, there are provided polypeptides, agonists, antagonists or inhibitors of such polypeptides, which can be used to modulate the action of such polypeptides, agonists, antagonists or inhibitors, e.g., in the treatment of arteriosclerosis, autoimmune and chronic inflammatory and infective diseases, histamine-mediated allergic reactions, hyper-eosinophilic syndrome, silicosis, sarcoidosis, inflammatory diseases of the lung, inhibition of IL-1 and TNF, aplastic anaemia, and myelodysplastic syndrome. Alternatively, such polypeptides can be used to inhibit production of IL-1 and TNF-$\alpha$ in any related diseases, e.g., to treat aplastic anemia, myelodysplastic syndrome, inflammatory diseases, diabetes, asthma and arthritis.

Such polypeptides, agonists, antagonists or inhibitors, can also be used to modulate (e.g., enhance or inhibit) the action of such polypeptides, for example, in the treatment of certain autoimmune diseases, atherosclerosis, chronic inflammatory and infectious diseases, histamine and IgE-mediated allergic reactions, prostaglandin-independent fever, bone marrow failure, cancers, silicosis, sarcoidosis, rheumatoid arthritis, shock, hyper-eosinophilic syndrome and fibrosis in the asthmatic lung.

Diagnostic Assays. In accordance with still another aspect of the present invention, there are provided diagnostic assays for detecting diseases related to the underexpression and overexpression of the polypeptides and for detecting mutations in the nucleic acid sequences encoding such polypeptides.

In accordance with yet another aspect of the present invention, there is provided a process for utilizing such polypeptides, or polynucleotides encoding such polypeptides, as research reagents for in vitro purposes related to scientific research, synthesis of DNA and manufacture of DNA vectors, for the purpose of developing therapeutics and diagnostics for the treatment of human disease.

The present invention also provides a screening method for identifying compounds capable of enhancing or inhibiting a cellular response induced by an Ck beta-11 and/or LAI-1 polypeptide, which involves contacting cells which express the Ck beta-11 and/or LAI-1 polypeptide with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

For a number of disorders, it is believed that significantly higher or lower levels of Ck beta-11 and/or LAI-1 gene expression can be detected in certain tissues or bodily fluids (e.g., serum, plasma, urine, synovial fluid or spinal fluid) taken from an individual having such a disorder, relative to a "standard" Ck beta-11 and/or LAI-1 gene expression level, i.e., the Ck beta-11 and/or LAI-1 expression level in tissue or bodily fluids from an individual not having the disorder. Thus, the invention provides a diagnostic method useful during diagnosis of a disorder, which involves: (a) assaying Ck beta-11 and/or LAI-1 gene expression level in cells or body fluid of an individual; (b) comparing the Ck beta-11 and/or LAI-1 gene expression level with a standard Ck beta-11 and/or LAI-1 gene expression level, whereby an increase or decrease in the assayed Ck beta-11 and/or LAI-1 gene expression level compared to the standard expression level is indicative of a disorder. Such disorders include leukemia, chronic inflammation, autoimmune diseases, solid tumors.

Pharmaceutical Compositions. The present invention also provides, in another aspect, pharmaceutical compositions comprising at least one of an Ck beta-11 and/or LAI-1: polynucleotide, probe, vector, host cell, polypeptide, fragment, variant, derivative, epitope bearing portion, antibody, antagonist, agonist.

Therapeutic Methods. In accordance with yet a further aspect of the present invention, there is provided a process for utilizing such polypeptides, or polynucleotides encoding such polypeptides for therapeutic purposes, for example, to protect bone marrow stem cells from chemotherapeutic agents during chemotherapy, to remove leukemic cells, to stimulate an immune response, to regulate hematopoiesis and lymphocyte trafficking, treatment of psoriasis, solid tumors, to enhance host defenses against resistant and acute and chronic infection, and to stimulate wound healing.

In accordance with yet a further aspect of the present invention, there is provided a process for utilizing such polypeptides, agonists, antagonists, or inhibitors, or polynucleotides encoding such polypeptides, for therapeutic purposes, for example, to treat solid tumors, chronic infections, leukemia, T-cell mediated auto-immune diseases, parasitic infections, psoriasis, asthma, allergy, to regulate hematopoiesis, to stimulate growth factor activity, to inhibit angiogenesis and to promote wound healing.

Alternatively or additionally, such treatment includes arteriosclerosis, autoimmune and chronic inflammatory and infective diseases, histamine-mediated allergic reactions, hyper-eosinophilic syndrome, silicosis, sarcoidosis, inflammatory diseases of the lung, inhibition of IL-1 and TNF, aplastic anaemia, and myelodysplastic syndrome. Alternatively, such polypeptides can be used to inhibit production of IL-1 and TNF-$\alpha$ in any related diseases, e.g., to treat aplastic anemia, myelodysplastic syndrome, inflammatory diseases, diabetes, asthma and arthritis.

Such polypeptides, agonists, antagonists or inhibitors, can also be used to treat (e.g., enhance or inhibit) the action of such polypeptides, agonists, antagonists or inhibitors, e.g., in the treatment of certain autoimmune diseases, atherosclerosis, chronic inflammatory and infectious diseases, histamine and IgE-mediated allergic reactions, prostaglandin-independent fever, bone marrow failure, cancers, silicosis, sarcoidosis, rheumatoid arthritis, shock, hyper-eosinophilic syndrome and fibrosis in the asthmatic lung.

An additional aspect of the invention is related to a method for treating an individual in need of an increased level of Ck beta-11 and/or LAI-1 activity in the body comprising administering to such an individual a composition comprising a therapeutically effective amount of an isolated Ck beta-11 and/or LAI-1 polypeptide, agonist, antagonist or inhibitor, of the invention.

A still further aspect of the invention is related to a method for treating an individual in need of a decreased level of Ck beta-11 and/or LAI-1 activity in the body comprising, administering to such an individual a composition comprising a therapeutically effective amount of an Ck beta-11 and/or LAI-1 polypeptide, agonist, antagonist or inhibitor, of the invention.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIG. 1 displays the cDNA sequence and corresponding deduced amino acid sequence of Ckβ-11. The initial 17 amino acids represent the leader sequence such that the mature polypeptide comprises 81 amino acids. The standard one-letter abbreviations for amino acids are used. Sequencing was performed using a 373 Automated DNA sequencer (Applied Biosystems, Inc.). Sequencing accuracy is expected to be greater than 97% accurate. However, in a baculovirus expression system, the first 21 amino acids were cleaved leaving a mature protein of Gly (22) - Ser (98).

FIG. 2 displays the CDNA sequence and corresponding deduced amino acid sequence of LAI-1. The initial 22 amino acids represent the leader sequence such that the mature polypeptide comprises 87 amino acids. The standard one-letter abbreviations for amino acids are used.

FIG. 6A: The IL1-β activated C monolayer was either pre-treated with LAI-1 (closed triangles) which was then washed away or had LAI-1 added during the adhesion assay (open circles) as described in FIG. 4. As shown, pre-treatment of the HUVEC monolayer with LAI-1 had no significant effect on the subsequent adhesion of PBMCS. Within this same assay, LAI-1 was still able to inhibit PBMC adhesion when present during the adhesion assay. FIG. 6B: Three separate donor PBMCs were pre-treated with LAI-1 at the concentrations indicated and the pre-treated cells monitored for their capacity to bind to an IL1-β activated HUVEC monolayer in the absence of any added LAI-1 during the assay. As shown, pre-treatment of the PBMCs with LAI-1 resulted in a reduction in binding ranging from 20 to 60% of that seen with the untreated PBMCS.

As shown in FIG. 7A, there was no effect on the percentage of cells which stained positive for CD29 (open symbols). However, the mean fluorescence intensity of the CD29 signal was reduced in both donors when the PBMCs were exposed to LAI-1 (closed symbols). This decrease in CD29 mean fluorescence was evident within a CD3 gated population of PBMCs but not in a CD20, CD56, or CD14 gated population. In addition, as shown in FIG. 7B, LAI-1 treatment caused an increase in the percentage of CD3$^+$/CD29-cells.

DESCRIPTION OF EMBODIMENTS

Figure 3:
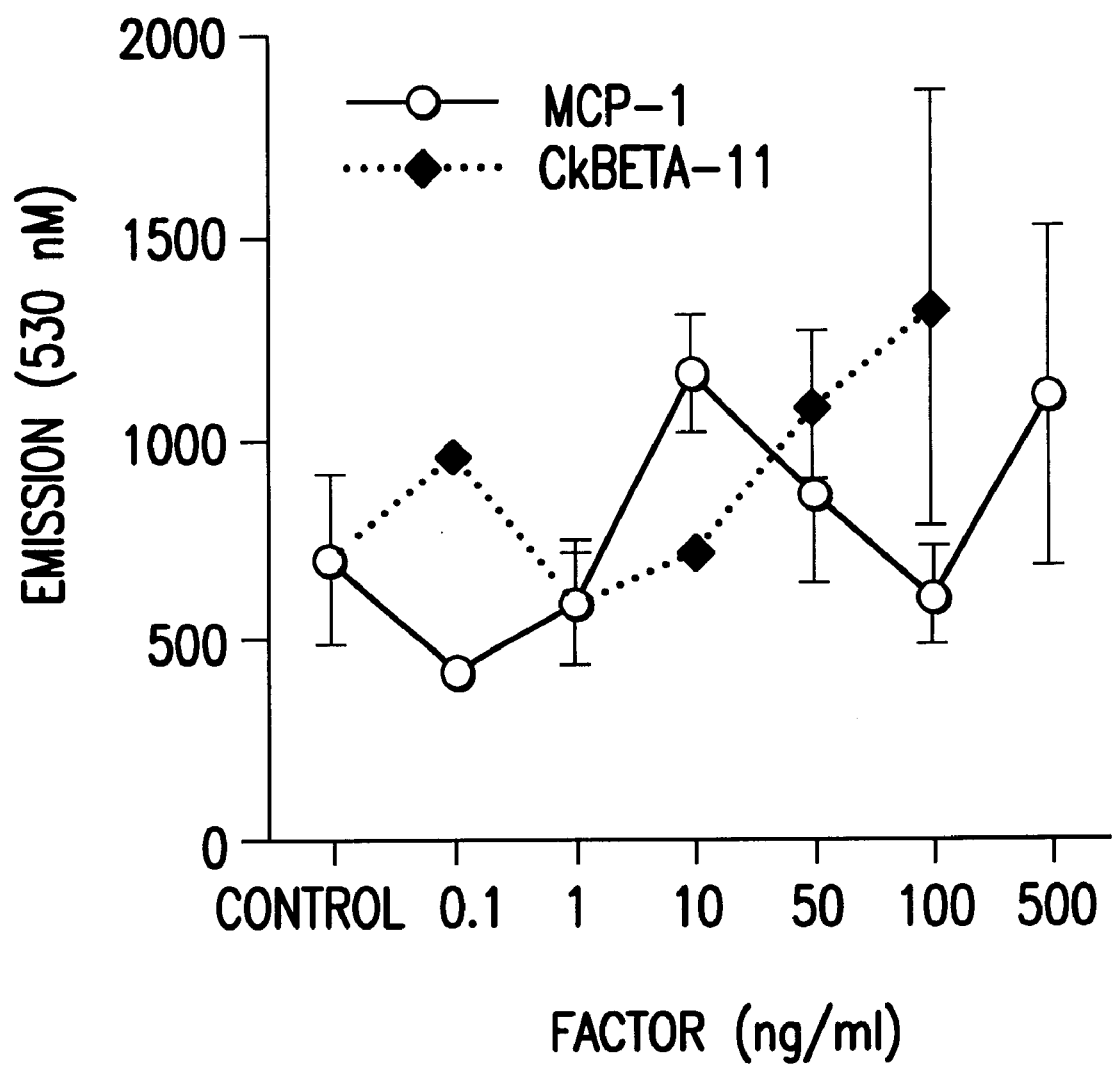
FIG. 3 shows data representing that Ck beta-11 affects chemotaxis with activated T-lymphocytes. The maximal effect of Ck-beta-11 was observed at 100 ng/ml.

The present invention provides diagnostic or therapeutic compositions and methods that utilize isolated polynucleotide molecules encoding polypeptides, or the polypeptides themselves, as: (i) a human leukocyte adhesion inhibitor-1 (LAI-1) polypeptides (previously termed chemokine α1(CKα1 or cka-1)); and/or (ii) human chemokine beta-11 (Ck beta-11) polypeptides, as are vectors, host cells and recombinant or synthetic methods for producing the same.

Ck beta-11 and/or LAI-11 Polynucleotides

In accordance with an aspect of the present invention, there are provided isolated nucleic acids (polynucleotides) which encode for the full-length or mature Ck beta-11 (FIG. 1) and/or LAI-1 polypeptide (FIG. 2) having the deduced amino acid sequence of, respectively, FIGS. 1 or 2 (SEQ ID NOS:2 or 4) and for the mature Ck beta-11 polypeptide encoded by the cDNA of the clone(s) deposited as ATCC Deposit No. 75948 on Nov. 11, 1994, and for the mature LAI-1 polypeptide encoded by the cDNA of the clone deposited as ATCC no. 75947, deposited on Nov. 11, 1994. The address of the American Type Culture Collection is 12301 Park Lawn Drive, Rockville, Md. 20852. The deposited clones are contained in the pBluescript SK(—) plasmid (Stratagene, LaJolla, Calif.).

The deposit(s) referred to herein will be maintained under the terms of the Budapest Treaty on the International Recognition of the Deposit of Micro-Organisms for Purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with description of sequences herein. A license can be required to make, use or sell the deposited materials, and no such license is hereby granted.

Polynucleotides encoding Ckβ-11 can be isolated from numerous human adult and fetal cDNA libraries, for example, a human fetal spleen cDNA library. Ckβ-11 is a member of the C—C branch of chemokines. It contains an open reading frame encoding a protein of 98 amino acid residues of which approximately the first 17 amino acids residues are the putative leader sequence such that the mature protein comprises 81 amino acids. The protein exhibits the highest degree of homology to the Rat RANTES polypeptide with 31% identity and 47% similarity over a stretch of 89 amino acids. It is also important that the four spatially conserved cysteine residues in chemokines are found in the polypeptides.

Polynucleotides encoding LAI-1 can be isolated from numerous human adult and fetal cDNA libraries, for example, human tonsils cDNA library. LAI-1 is a member of the C—X—C branch of chemokines. It contains an open reading frame encoding a protein of 109 amino acid residues of which approximately the first 22 amino acids residues are the putative leader sequence such that the mature protein comprises 87 amino acids. The protein exhibits the highest degree of homology to interleukin-8 from Sheep (Ovis Aries) with 31% identity and 80% similarity over a stretch of 97 amino acids. It is also important that the four spatially conserved cysteine residues in chemokines are found in the polypeptides.

The polynucleotides of the present invention can be in the form of RNA or in the form of DNA, which DNA includes cDNA, genomic DNA, and synthetic DNA. The DNA can be double-stranded or single-stranded, and if single stranded can be the coding strand or non-coding (anti-sense) strand. The coding sequence which encodes the mature polypeptides can be identical to the coding sequence shown in FIGS. 1 and 2 (SEQ ID NOS: 1 and 3, respectively) or that of the deposited clone(s) or can be a different coding sequence which coding sequence, as a result of the redundancy or degeneracy of the genetic code, encodes the same, mature polypeptides as the DNA of FIG. 1 and 2 (SEQ ID NOS: 1 and 3) or the deposited cDNAs.

The polynucleotides which encode for the mature polypeptides of FIGS. 1 and 2 (SEQ ID NOS: 2 and 4) or for the mature polypeptides encoded by the deposited cDNA can include: only the coding sequence for the mature polypeptide; the coding sequence for the mature polypeptides and additional coding sequence such as a leader or secretory sequence or a proprotein sequence; the coding sequence for the mature polypeptides (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes only coding sequence for the polypeptide as well as a polynucleotide which includes additional coding and/or non-coding sequence.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein can contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO: 1 or 3, as set forth using deoxyribonucleotide abbreviations, is intended to indicate an RNA molecule having a sequence in which each deoxyribonucleotide A, G or C of SEQ ID NOS: 1 and/or 2 have been replaced by the corresponding ribonucleotide A, G or C, and each deoxyribonucleotide T has been replaced by a ribonucleotide U.

Using the information provided herein, such as the nucleotide sequence in FIGS. 1 and/or 2, a nucleic acid molecule of the present invention encoding an Ck beta-11 and/or LAI-1 (respectively) polypeptide can be obtained using standard cloning and screening procedures, such as those for cloning cDNAs using mRNA as starting material.

The present invention further relates to variants of the hereinabove described polynucleotides which encode for fragments, analogs and derivatives of the polypeptide having the deduced amino acid sequence of FIGS. 1 and 2 (SEQ ID NOS:2 and 4) or the polypeptides encoded by the cDNA of the deposited clone(s). The variants of the polynucleotides can be a naturally occurring allelic variant of the polynucleotides or a non-naturally occurring variant of the polynucleotides.

The present invention also includes polynucleotides encoding the same mature polypeptides as shown in FIGS. 1 and 2 (SEQ ID NOS:2 and 4) or the same mature polypeptides encoded by the cDNA of the deposited clone(s) as well as variants of such polynucleotides which variants encode for a fragment, derivative or analog of the polypeptides of FIGS. 1 and 2 (SEQ ID NOS:2 and 4) or the polypeptides encoded by the cDNA of the deposited clone (s). Such nucleotide variants include deletion variants, substitution variants and addition or insertion variants.

As hereinabove indicated, the polynucleotide can have a coding sequence which is a naturally occurring allelic variant of the coding sequence shown in FIGS. 1 and 2 (SEQ ID NOS:2 and 4) or of the coding sequence of the deposited clone(s). As known in the art, an allelic variant is an alternate form of a polynucleotide sequence which can have a substitution, deletion or addition of one or more nucleotides, which does not substantially alter the function of the encoded polypeptide.

The present invention also includes polynucleotides, wherein the coding sequence for the mature polypeptides can be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotides of the present invention can encode for a mature protein, or for a protein having a prosequence or for a protein having both a prosequence and a presequence (leader sequence).

The polynucleotides of the present invention can also have the coding sequence fused in frame to a marker sequence which allows for purification of the polypeptides of the present invention. The marker sequence can be a hexa-histidine tag supplied by a pQE-9 vector to provide for purification of the mature polypeptides fused to the marker in the case of a bacterial host, or, for example, the marker sequence can be a hemagglutinin (HA) tag when a mammalian host, e.g. COS-7 cells, is used. The HA tag corresponds to an epitope derived from the influenza hemagglutinin protein (Wilson, I., et al., *Cell,* 37:767 (1984)).

The term "gene" means the segment of DNA involved in producing a polypeptide chain; it includes regions preceding and following the coding region (leader and trailer) as well as intervening sequences (introns) between individual coding segments (exons).

As indicated, nucleic acid molecules of the present invention can be in the form of RNA, such as mRNA, or in the form of DNA, including, for instance, cDNA and genomic DNA obtained by cloning or produced synthetically. The DNA can be double-stranded or single-stranded. Single-stranded DNA or RNA can be the coding strand, also known as the sense strand, or it can be the non-coding strand, also referred to as the anti-sense strand.

The term "isolated" means that the material is removed from its original environment (e.g., the natural environment if it is naturally occurring). For example, a naturally-occurring polynucleotides or polypeptides present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) for a Ck beta-11 and/or LAI-1 cDNA; DNA molecules comprising the coding sequence for a mature Ck beta-11 and/or LAI-1 protein; and DNA molecules which comprise a sequence substantially different from those described above but which, due to the degeneracy of the genetic code, still encode an Ck beta-11 and/or LAI-1 polypeptide. Of course, the genetic code is well known in the art. Thus, it would be routine for one skilled in the art to generate the degenerate variants described above.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNAs of FIG. 1 and 2 (SEQ ID NO:1 and 3) or the deposited cDNA(s).

Alternatively, the polynucleotide can have at least 20 bases, preferably 30 bases, and more preferably at least 50 bases which hybridize to a polynucleotide of the present invention and which has an identity thereto, as hereinabove described, and which can or can not retain activity. For example, such polynucleotides can be employed as probes for the polynucleotide of SEQ ID NO:1 and 3, for example, for recovery of the polynucleotide or as a diagnostic probe or as a PCR primer.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 75947 (LAI-1) or ATCC Deposit 75948 (Ck beta-11). By "stringent hybridization conditions" is intended, as a non-limiting example, overnight incubation at 42° C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 g/ml denatured, sheared salmon sperm DNA, followed by washing the filters in O.ix SSC at about 65° C. Similar stringent conditions are well-known in the art.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g. the deposited cDNA clone), for instance, a portion 50–750 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIG. 2 (LAI-1); and/or FIG. 1 (Ck beta-11). By a portion of a polynucleotide of "at least 20 nt in length," for example, is intended 20 or more contiguous nucleotides from the nucleotide sequence of the reference polynucleotide. As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a Ck beta-11 and/or LAI-1 cDNA clones have been deposited and its determined nucleotide sequence provided, generating polynucleotides which hybridize to a portion of the Ck beta-11 and/or LAI-1 cDNA molecules would be routine to the skilled artisan. For example, restriction endonuclease cleavage or shearing by sonication of a Ck beta-11 and/or LAI-1 cDNA clone could easily be used to generate DNA portions of various sizes which are polynucleotides that hybridize, respectively, to a portion of the Ck beta-11 and/or LAI-1 cDNA molecules.

Alternatively, the hybridizing polynucleotides of the present invention could be generated synthetically according to known techniques. Of course, a polynucleotide which hybridizes only to a poly A sequence (such as the 3' terminal poly(A) tract of a cDNA, or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g. practically any double-stranded CDNA clone).

As indicated, nucleic acid molecules of the present invention which encode an Ck beta-11 and/or LAI-1 polypeptide can include, but are not limited to those encoding the amino acid sequence of the mature polypeptide, by itself; the coding sequence for the mature polypeptide and additional sequences, such as those encoding the leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide can be fused to a marker sequence, such as a sequence encoding a peptide which facilitates purification of the fused polypeptide. In certain preferred embodiments of this aspect of the invention, the marker amino acid sequence is a hexahistidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexahistidine provides for convenient purification of the fusion protein. The "HA" tag is another peptide useful for purification which corresponds to an epitope derived from the influenza hemagglutinin protein, which has been described by Wilson et al., Cell 37: 767 (1984). As discussed below, other such fusion proteins include at least one of an Ck beta-11 and/or LAI-1 polypeptide or fragment fused to Fc at the N- or C-terminus.

The present invention further relates to variants of the nucleic acid molecules of the present invention, which encode portions, analogs or derivatives of an Ck beta-11 and/or LAI-1 polypeptide. Variants can occur naturally, such as a natural allelic variant. By an "allelic variant" is intended one of several alternate forms of a gene occupying a given locus on a chromosome of an organism. Genes V, Lewin, B., ed., Oxford University Press, New York (1994). Non-naturally occurring variants can be produced using art-known mutagenesis techniques.

Such variants include those produced by nucleotide substitutions, deletions or additions. The substitutions, deletions or additions can involve one or more nucleotides. The variants can be altered in coding regions, non-coding regions, or both. Alterations in the coding regions can produce conservative or non-conservative amino acid substitutions, deletions or additions. Especially preferred among these are silent substitutions, additions and deletions, which do not alter the properties and activities of an Ck beta-11 and/or LAI-1 polypeptide or portions thereof. Also especially preferred in this regard are conservative substitutions. Most highly preferred are nucleic acid molecules encoding the mature protein or the mature amino acid sequence encoded by the deposited cDNA clone, as described herein.

Ck beta-11 and/or LAI-1 Homolog Polynucleotides. The present invention is further directed to polynucleotides having at least a 70% identity, preferably at least 90% and more preferably at least a 95% identity to a polynucleotide which encodes the polypeptide of SEQ ID NO:2 or 4, as well as fragments thereof, which fragments have at least 30 bases and preferably at least 50 bases and to polypeptides encoded by such polynucleotides.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding an Ck beta-11 and/or LAI-1 polypeptide or fragment, having an amino acid sequence of FIG. 1 and/or FIG. 2, respectively, including the predicted leader sequence; (b) a nucleotide sequence encoding the mature Ck beta-11 and/or LAI-1 polypeptide (full-length polypeptide with the leader removed); (c) a nucleotide sequence encoding the full-length polypeptide having the complete amino acid sequence including the leader encoded by the deposited cDNA clone; (d) a nucleotide sequence encoding the mature polypeptide having the amino acid sequence encoded by the deposited cDNA clone; or (e) a nucleotide sequence complementary to any of the nucleotide sequences in (a), (b), (c) or (d).

By a polynucleotide having a nucleotide sequence at least, for example, 95% "identical" to a reference nucleotide sequence encoding an Ck beta-11 and/or LAI-1 polypeptide is intended that the nucleotide sequence of the polynucleotide is identical to the reference sequence except that the polynucleotide sequence can include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1 or 3, or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As one of ordinary skill would appreciate, due to the possibilities of sequencing errors discussed above, as well as the variability of cleavage sites for leaders in different known proteins, the actual LAI-1 polypeptide encoded by the deposited cDNA comprises about 87 amino acids, but can be anywhere in the range of 79–103 amino acids; and the actual leader sequence of this protein is about 22 amino acids, but can be anywhere in the range of about 15 to about 30 amino acids.

As one of ordinary skill would appreciate, due to the possibilities of sequencing errors discussed above, as well as the variability of cleavage sites for leaders in different known proteins, the actual Ck beta-11 polypeptide encoded by the deposited cDNA comprises about 81 amino acids, but can be anywhere in the range of 70–95 amino acids; and the actual leader sequence of this protein is about 17 amino acids, but can be anywhere in the range of about 10 to about 25 amino acids.

NucleicAcid Probes. Such isolated molecules, particularly DNA molecules, are useful as probes for gene mapping, by in situ hybridization with chromosomes, and for detecting expression of a Ck beta-11 and/or LAI-1 gene in human or other animal tissue, for instance, by Northern blot analysis. The present invention is further directed to fragments of the isolated nucleic acid molecules described herein. By a fragment of an isolated nucleic acid molecule having the nucleotide sequence of the deposited Ck beta-11 and/or LAI-1 cDNAs, or a nucleotide sequence shown in any or all of FIGS. 1 and 2 (SEQ ID NOS: 1 and 3), respectively, is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–500 nt in length are also useful according to the present invention as are fragments corresponding to most, if not all, of a nucleotide sequence of the deposited Ck beta-11 and/or LAI-1 cDNAs, or as shown in FIGS. 1 and 2 (SEQ ID NOS: 1 and 3). By a fragment at least 20 nt in length, for example, is intended fragments which include 20 or more contiguous bases from the nucleotide sequence of the deposited cDNA or the nucleotide sequence as shown in FIGS. 1 and 2 (SEQ ID NOS:1 and 3). Since the gene has been deposited and the nucleotide sequences shown in FIGS. 1 and 2 (SEQ ID NOS:1 and 3) are provided, generating such DNA fragments would be routine to the skilled artisan. For example, restriction endonuclease cleavage or shearing by sonication could easily be used to generate fragments of various sizes. Alternatively, such fragments could be generated synthetically.

Fragments of the full length gene of the present invention can be used as a hybridization. probe for a cDNA library to isolate the full length cDNA and to isolate other cDNAs which have a high sequence similarity to the gene or similar biological activity. Probes of this type preferably have at least 30 bases and can contain, for example, 50 or more bases. The probe can also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

Vectors and Host Cells. The present invention also relates to vectors which include the isolated DNA molecules of the present invention, host cells which are genetically engineered with the recombinant vectors, and the production of Ck beta-11 and/or LAI-1 polypeptides, variants, mutants or fragments thereof by recombinant techniques.

Recombinant constructs can be introduced into host cells using well known techniques such infection, transduction, transfection, transvection, electroporation and transformation. The vector can be, for example, a phage, plasmid, viral or retroviral vector. Retroviral vectors can be replication competent or replication defective. In the latter case, viral propagation generally will occur only in complementing host cells.

The polynucleotides can be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

Preferred are vectors comprising cis-acting control regions to the polynucleotide of interest. Appropriate trans-acting factors can be supplied by the host, supplied by a complementing vector or supplied by the vector itself upon introduction into the host.

In certain preferred embodiments in this regard, the vectors provide for specific expression, which can be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, (Qiagen); pBS vectors, pD10, Phagescript vectors, pBluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the E. coli lad and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

Transcription of the DNA encoding the polypeptides of the present invention by higher eukaryotes can be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the LAI-1 and/or Ck beta-11 genes. The culture conditions, such as temperature, pH and the like, are those previously used with the host cell selected for expression, and will be apparent to the ordinarily skilled artisan.

The polynucleotides of the present invention can be employed for producing polypeptides by recombinant techniques. Thus, for example, the polynucleotide sequence can be included in any one of a variety of expression vehicles, in particular vectors or plasmids for expressing a polypeptide. Such vectors include chromosomal, nonchromosomal and synthetic DNA sequences, e.g. derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector can be used as long they are replicable and viable in the host.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there can be mentioned: LTR or SV40 promoter, the E. coli. lac or trp, the phage lambda PL promoter and other promoters known to control expression of genes in prokaryotic or eukaryotic cells or their viruses. The expression vector also contains a ribosome binding site for translation initiation and a transcription terminator. The vector can also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, can be employed to transform an appropriate host to permit the host to express the protein.

As representative examples of appropriate hosts, there can be mentioned: bacterial cells, such as E. coli, Streptomyces, Salmonella Typhimurium; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXTI, pSG (Stratagene) pSVK3, pBPV, pMSG, pSVL (Pharmacia). However, any other plasmid or vector can be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacd, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g. the ampicillin resistance gene of E. coli and S. cerevisiae TRPL gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g. stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others can also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced by appropriate means (e.g. temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites can be used to provide the required nontranscribed genetic elements. Polypeptides and Polypeptide Fragments. The invention further provides an isolated Ck beta-11 and/or LAI-1 polypeptide having the amino acid sequence encoded by the deposited cDNA, or the amino acid sequence in FIGS. 1 or 2 (SEQ ID NO:2 or 4, respectively), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

By "a polypeptide having Ck beta-11 activity" is intended polypeptides exhibiting activity similar, but not necessarily identical, to an activity of the Ck beta-11 protein of the invention (either the full-length protein or, preferably, the mature protein), as measured in a particular biological assay. Ck beta-11 protein activity can be measured using the chemotaxis assay disclosed in Example 8, infra.

Thus, "a polypeptide having Ck beta-11 protein activity" includes polypeptides that exhibit Ck beta-11 activity, in the above-described assay. Although the degree of activity need not be identical to that of the Ck beta-11 protein, preferably, "a polypeptide having Ck beta-11 protein activity" will exhibit substantially similar activity as compared to the Ck beta-11 protein (i.e., the candidate polypeptide will exhibit greater activity or not more than about twenty-fold less and, preferably, not more than about ten-fold less activity relative to the reference Ck beta-11 protein).

By "a polypeptide having LAI-1 activity" is intended polypeptides exhibiting activity similar, but not necessarily identical, to an activity of the LAI-1 protein of the invention (either the full-length protein or, preferably, the mature protein), as measured in a particular biological assay. For example, LAI-1 protein activity can be measured using the leukocyte adhesion assay as described in Example 10, the angiogenesis assay of Example 11, or the chemotaxis assay as described in Example 9, infra.

Thus, "a polypeptide having LAI-1 protein activity" includes polypeptides that exhibit LAI-1 activity, in the above-described assays. Although the degree of activity need not be identical to that of the LAI-1 protein, preferably, "a polypeptide having LAI-1 protein activity" will exhibit substantially similar activity as compared to the LAI-1 protein (i.e., the candidate polypeptide will exhibit greater activity or not more than about twenty-fold less and, preferably, not more than about ten-fold less activity relative to the reference LAI-1 protein).

The present invention further relates to Ck beta-11 and/or LAI-1 polypeptides which have the deduced amino acid sequence of FIGS. 1 and 2 (SEQ ID NOS: 2 and 4) or which have the amino acid sequence encoded by the deposited cDNA, as well as fragments, analogs and derivatives of such polypeptide.

The terms "fragment," "derivative" and "analog" when referring to the polypeptides of FIGS. 1 and 2 (SEQ ID NOS: 2 and 4) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptides of the present invention can be a recombinant polypeptide, a natural polypeptide or a synthetic polypeptide, preferably a recombinant polypeptide.

The fragment, derivative or analog of the polypeptides of FIGS. 1 and 2 (SEQ ID NOS: 2 and 4) or that encoded by the deposited cDNA can be (i) one in which one or more of the amino acid residues are substituted with a conserved or non-conserved amino acid residue (preferably a conserved amino acid residue) and such substituted amino acid residues is or is not be one encoded by the genetic code, or (ii) one in which one or more of the amino acid residues includes a substituent group, or (iii) one in which the mature polypeptides are fused with another compound, such as a compound to increase the half-life of the polypeptide (for example, polyethylene glycol), or (iv) one in which the additional amino acids are fused to the mature polypeptides, such as a leader or secretory sequence or a sequence which is employed for purification of the mature polypeptides or a proprotein sequence. Such fragments, derivatives and analogs are deemed to be within the scope of those skilled in the art from the teachings herein.

The polypeptides of the present invention are preferably provided in an isolated form, and preferably are purified to homogeneity.

The polypeptides of the present invention include the polypeptide of SEQ ID NO:2 and 4 (in particular the mature polypeptide) as well as polypeptides which have at least 70% similarity (preferably at least 70% identity) to the polypeptide of SEQ ID NO:2 and 4 and more preferably at least 90% similarity (more preferably at least 90% identity) to the polypeptide of SEQ ID NO: 2 and 4 and still more preferably at least 95% similarity (still more preferably at least 95% identity) to the polypeptide of SEQ ID NO:2 and 4 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA (ATCC 75948) or the nucleic acid sequence shown in FIG. 1 (SEQ ID NO:1) will encode apolypeptide "having Ck beta-1 I protein activity." One of ordinary skill in the art will also immediately recognize that a large number of the nucleic acid molecules having a sequence at least 90%, 95%, 96%, 97%, 98%, or 99% identical to the nucleic acid sequence of the deposited cDNA (ATCC 75947) or the nucleic acid sequence shown in FIG. 2 (SEQ ID NO:3) will encode a polypeptide "having LAI-1 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Ck beta-11 and/or LAI-1 protein activity. This is because the skilled artisan is fully aware of amino acid substitutions that are either less likely or not likely to significantly effect protein function (e.g. replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Fragments or portions of the polypeptides of the present invention can be employed for producing the corresponding full-length polypeptide by peptide synthesis; therefore, the fragments can be employed as intermediates for producing the full-length polypeptides. Fragments or portions of the polynucleotides of the present invention can be used to synthesize full-length polynucleotides of the present invention.

For secretion of the translated protein into the lumen of the endoplasmic reticulum, into the periplasmic space or into the extracellular environment, appropriate secretion signals can be incorporated into the expressed polypeptide. The signals can be endogenous to the polypeptide or they can be heterologous signals.

The polypeptide can be expressed in a modified form, such as a fusion protein, and can include not only secretion signals, but also additional heterologous functional regions. For instance, a region of additional amino acids, particularly charged amino acids, can be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5- has been fused with Fc portions for the purpose of high-throughput screening assays to identify antagonists of hIL-5. See, D. Bennett et al., *Journal of Molecular Recognition, Vol.* 8:52–58 (1995) and K. Johanson et al., *The Journal of Biological Chemistry, Vol.* 270, No. 16:9459-9471 (1995).

The Ck beta-11 and/or LAI-1 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention can be glycosylated or can be non-glycosylated. In addition, polypeptides of the invention can also include an initial modified methionine residue, in some cases as a result of host-mediated processes.

Ck beta-11 and/or LAI-1 Polypeptide Variants. It will be recognized in the art that some amino acid sequences of the Ck beta-11 and/or LAI-1 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue can be completely unimportant if the alteration occurs at a non-critical region of the protein.

Thus, the invention further includes variations of an Ck beta-11, LAI-1 polypeptide which show, respectively, substantial Ck beta-11 and/or LAI-1 polypeptide activity or which include regions, respectively, of an Ck beta-11 and/or LAI-1 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Preferred substitutions are at positions 1–28, 31–70 and/or 72–89 of Ck beta-11(FIG. 1; SEQ ID NO:2); and at positions 1–29, 35–75 and/or 77–109 of LAI-1 (FIG. 2; SEQ ID NO:4).

Of additional special interest are also substitutions of charged amino acids with another charged amino acid or with neutral amino acids. This can result in proteins with improved characteristics such as less aggregation. Prevention of aggregation is highly desirable. Aggregation of proteins cannot only result in a reduced activity but be problematic when preparing pharmaceutical formulations because they can be immunogenic (Pinckard et al., Clin. Exp. Immunol. 2:331–340 (1967), Robbins et al., Diabetes 36: 838–845 (1987), Cleland et al., Crit. Rev. Therapeutic Drug Carrier Systems 10:307–377 (1993).

The replacement of amino acids can also change the selectivity of the binding to cell surface receptors. Ostade et al., Nature 361: 266–268 (1993), described certain TNF alpha mutations resulting in selective binding of TNF alpha to only one of the two known TNF receptors.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990). The number of amino acid substitutions a skilled artisan would make depends on several factors, including those described above and below. Generally speaking the number of substitutions for any given LAI-1 or Ckβ-1 polypeptide will not be more than 50, 40, 30, 20, 10, 5, or 3, depending on the objective.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Ck beta-11 Variants. In order to improve or alter the characteristics of the Ck beta-11 polypeptide(s), protein engineering can be employed. Recombinant DNA technology known to those skilled in the art can be used to create novel proteins. Muteins and deletions or fusion proteins can show, e.g., enhanced activity or increased stability. In addition, they could be purified in higher yields and show better solubility at least under certain purification and storage conditions. Set below are additional examples of mutations that can be constructed.

Ck beta-11 Aminoterminal and carboxyterminal deletions: Interferon gamma shows up to ten times higher activities by deleting 8–10 amino acid residues from the carboxy terminus of the protein (Dobeli et al., J. of Biotechnology 7:199–216 (1988). Ron et al., J. Biol. Chem., 268(4):2984–988 (1993) reported modified KGF proteins that had heparin binding activity even if 3, 8, or 27 amino terminal amino acid residues were missing. Many other examples are known to anyone skilled in the art.

Ck beta-11 deletion variants include deletions of 1–28 from the N-terminus and 1–27 from the C-terminus (FIG. 1, SEQ ID NO:2). Particularly preferred Ck beta-11 polypeptides are shown below:

| | |
|---|---|
| Pro (18)-Ser (98) | Pro (18)-Thr (89) |
| Thr (19)-Ser (98) | Pro (18)-Arg (88) |
| Leu (20)-Ser (98) | Pro (18)-Gln (87) |
| Ser (21)-Ser (98) | Pro (18)-Leu (86) |
| Gly (22)-Ser (98) | Pro (18)-Arg (85) |
| Thr (23)-Ser (98) | Pro (18)-Gln (84) |
| Asn (24)-Ser (98) | Pro (18)-Ile (83) |
| Asp (25)-Ser (98) | Pro (18)-Ile (82) |
| Ala (26)-Ser (98) | Pro (18)-Arg (81) |
| Glu (27)-Ser (98) | Pro (18)-Glu (80) |
| Asp (28)-Ser (98) | Pro (18)-Val (79) |
| Pro (18)-Cys (71) | Pro (18)-Trp (78) |
| Pro (18)-Ser (97) | Pro (18)-Pro (77) |
| Pro (18)-Arg (96) | Pro (18)-Gln (76) |
| Pro (18)-Arg (95) | Pro (18)-Asp (75) |
| Pro (18)-Lys (94) | Pro (18)-Pro (74) |
| Pro (18)-Met (93) | Pro (18)-Pro (73) |
| Pro (18)-Lys (92) | Pro (18)-Ala (72) |
| Pro (18)-Ala (91) | Ser (21)-Lys (94) |
| Pro (18)-Ser (90) | Ser (21)-Lys (92) |
| Gly (22)-Cys (71) | Gly (22)-Ile (83) |
| Gly (22)-Ser (97) | Gly (22)-Ile (82) |
| Gly (22)-Arg (96) | Gly (22)-Arg (81) |
| Gly (22)-Arg (95) | Gly (22)-Glu (80) |
| Gly (22)-Lys (94) | Gly (22)-Val (79) |
| Gly (22)-Met (93) | Gly (22)-Trp (78) |
| Gly (22)-Lys (92) | Gly (22)-Pro (77) |
| Gly (22)-Ala (91) | Gly (22)-Gln (76) |
| Gly (22)-Ser (90) | Gly (22)-Asp (75) |
| Gly (22)-Thr (89) | Gly (22)-Pro (74) |
| Gly (22)-Arg (88) | Gly (22)-Pro (73) |
| Gly (22)-Gln (87) | Gly (22)-Ala (72) |
| Gly (22)-Leu (86) | |
| Gly (22)-Arg (85) | |
| Gly (22)-Gln (84) | |

Substitution of amino acids: A further aspect of the present invention also includes the substitution of amino acids. Of special interest are conservative amino acid substitutions that do not significantly affect the folding of the protein. Examples of conservative amino acid substitutions known to those skilled in the art are set forth Table 1, above.

Of additional special interest are also substitutions of charged amino acids with another charged amino acid or with neutral amino acids. This can result in proteins with improved characteristics such as less aggregation. Prevention of aggregation is highly desirable. Aggregation of proteins cannot only result in a reduced activity but be problematic when preparing pharmaceutical formulations because they can be immunogenic (Pinckard et al., Clin. Exp. Immunol. 2:331–340 (1967), Robbins et al., Diabetes 36:838–845 (1987), Cleland et a., Crit. Rev. Therapeutic Drug Carrier Systems 10:307–377 (1993).

The Ck beta-11 protein can contain one or several amino acid substitutions, deletions or additions, either from natural mutation or human manipulation. Preferred substitutions are at positions 1–28, 31–70 and 72–89 of Ck beta-11 (FIG. 1; SEQ ID NO:2). Non-limiting examples of some preferred mutations are:

| | |
|---|---|
| Ala (17) Met | Asp (53) Ala |
| Pro (18) Met | Asp (53) Gly |
| Asp (53) Ser | Asp (53) Ala |
| Asp (53) Thr | |
| Asp (53) Met | |

LAI-1 Variants. In order to improve or alter the characteristics of the LAI-1 polypeptide(s), protein engineering can be employed. Recombinant DNA technology known to those skilled in the art can be used to create novel proteins. Muteins and deletions or fusion proteins can show, e.g., enhanced activity or increased stability. In addition, they could be purified in higher yields and show better solubility at least under certain purification and storage conditions. Set below are examples of mutations that can be constructed.

LAI-1 Amino terminal and carboxyterminal deletions: Interferon gamma shows up to ten times higher activities by deleting 8–10 amino acid residues from the carboxy terminus of the protein (Döbeli et al., J. of Biotechnology 7:199–216 (1988). Ron et al., J. Biol. Chem., 268(4):2984–2988 (1993) reported modified KGF proteins that had heparin binding activity even if 3, 8, or 27 amino terminal amino acid residues were missing. Many other examples are known to anyone skilled in the art.

LAI-1 deletion variants include deletions of 1–29 from the N-terminus and 1–33 from the C-terminus (FIG. 2, SEQ ID NO:4). Particularly preferred variants of LAI-1 polypeptides of some preferred mutations are:

| | |
|---|---|
| Gly (22)-Pro (109) | Tyr (28)-Phe (104) |
| Val (23)-Pro (109) | Thr (29)-Val (103) |
| Leu (24)-Pro (109) | Val (23)-Pro (102) |
| Glu (25)-Pro (109) | Val (23)-Cys (76) |
| Val (26)-Pro (109) | Val (23)-Val (101) |
| Tyr (27)-Pro (109) | Val (23)-Pro (100) |
| Tyr (28)-Pro (109) | Val (23)-Leu (99) |
| Thr (29)-Pro (109) | Val (23)-Thr (98) |
| Ser (30)-Pro (109) | Val (23)-Ser (97) |
| Gly (22)-Pro (109) | Val (23)-Ser (96) |
| Val (23)-Ile (109) | Val (23)-Ser (95) |
| Leu (24)-Ile (108) | Val (23)-Arg (94) |
| Glu (25)-Lys (107) | Val (23)-Lys (93) |
| Val (26)-Arg (106) | Val (23)-Arg (92) |
| Tyr (27)-Lys (105) | Val (23)-Leu (91) |
| Val (23)-Val (90) | Val (23)-Gln (80) |
| Val (23)-Glu (89) | Val (23)-Pro (79) |
| Val (23)-Met (88) | Val (23)-Asp (78) |
| Val (23)-Met (87) | Val (23)-Val (77) |
| Val (23)-Arg (86) | Ser (30)-Lys (107) |
| Val (23)-Gln (85) | Ser (30)-Lys (105) |
| Val (23)-Ile (84) | Ser (30)-Lys (93) |
| Val (23)-Trp (83) | Ser (30)-Cys (76) |
| Val (23)-Glu (82) | |
| Val (23)-Ala (81) | |

An LAI-1 polypeptide can contain one or several amino acid substitutions, deletions or additions, either from natural mutation or human manipulation. Preferred substitutions are at positions 1–29, 35–75 and 77–109 of LAI-1 (FIG. 2; SEQ ID NO:4). Non-limiting examples of some preferred mutations are:

Gly (22) Met

Val (23) Met

The polypeptides of the present invention are preferably provided in an isolated form, and preferably are substantially purified. A recombinantly produced version of the Ck beta-11 and/or LAI-1 polypeptide can be substantially purified by the one-step method described in Smith and Johnson, *Gene* 67:31–40 (1988).

The polypeptides of the present invention include the polypeptide encoded by the deposited cDNA including the leader, the mature polypeptide encoded by the deposited the CDNA minus the leader (i.e., the mature protein), the Ck beta-1 I polypeptide of FIG. 1 (SEQ ID NO:2) or the LAI-1 polypeptide of FIG. 2 (SEQ ID NO:4) including the leader, Ck beta-11 the polypeptide of FIG. 1 (SEQ ID NO:2), or the LAI-1 polypeptide of FIG. 2 (SEQ ID NO:4) minus the leader, as well as polypeptides which have at least 90% similarity, more preferably at least 95% similarity, and still more preferably at least 96%, 97%, 98% or 99% similarity to those described above. Further polypeptides of the present invention include polypeptides at least 80% identical, more preferably at least 90% or 95% identical, still more preferably at least 96%, 97%, 98% or 99% identical to the polypeptide encoded by the deposited cDNA, to the Ck beta-11 polypeptide of FIG. 1 (SEQ ID NO:2) or the LAI-1 polypeptide of FIG. 2 (SEQ ID NO:4) and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482–489, 1981) to find the best segment of similarity between two sequences.

By a polypeptide having an amino acid sequence at least, for example, 95% "identical" to a reference amino acid sequence of an Ck beta-11 and/or LAI-1 polypeptide is intended that the amino acid sequence of the polypeptide is identical to the reference sequence except that the polypeptide sequence can include up to five amino acid alterations per each 100 amino acids of the reference amino acid of the Ck beta-11 and/or LAI-1 polypeptide. In other words, to obtain a polypeptide having an amino acid sequence at least 95% identical to a reference amino acid sequence, up to 5% of the amino acid residues in the reference sequence can be deleted or substituted with another amino acid, or a number of amino acids up to 5% of the total amino acid residues in the reference sequence can be inserted into the reference sequence. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 (SEQ ID NO:2) or FIG. 2 (SEQ ID NO:4), or to the amino acid sequence encoded by deposited CDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting Ck beta-11 and/or LAI-1 protein expression as described below or as agonists and antagonists capable of enhancing or inhibiting Ck beta-11 and/or LAI-1 protein function. Further, such polypeptides can be used in the yeast two-hybrid system to "capture" Ck beta-11 and/or LAI-1 protein binding proteins which are also candidate agonist and antagonist according to the present invention. The yeast two hybrid system is described in Fields and Song, *Nature* 340:245–246 (1989). Ck beta-11 and/or LAI-1 Epitope-Bearing Polypeptides. In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, e.g., Sutcliffe, J. G., Shinnick, T. M., Green, N. and Learner, R. A., Science 219:660–666 (1983).

Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HAI polypeptide chain, induced antibodies that reacted with the HAI protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides can be used for tracking the fate of various regions of a protein precursor which undergoes post-translational processing. The peptides and anti-peptide antibodies can be used in a variety of qualitative or quantitative assays for the mimicked protein, for instance in competition assays since it has been shown that even short peptides (e.g. about 9 amino acids) can bind and displace the larger peptides in immunoprecipitation assays. See, for instance, Wilson et al., Cell 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention can be produced by any conventional means for making peptides or polypeptides including recombinant means using nucleic acid molecules of the invention. For instance, a short epitope-bearing amino acid sequence can be fused to a larger polypeptide which acts as a carrier during recombinant production and purification, as well as during immunization to produce anti-peptide antibodies. Epitope-bearing peptides also can be synthesized using known methods of chemical synthesis. For instance, Houghten has described a simple method for synthesis of large numbers of peptides, such as 10–20 mg of 248 different 13 residue peptides representing single amino acid variants of a segment of the HAI polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-perneable packets, enabling the optimal use of the many identical repetitive steps involved in solid-phase methods. A completely manual procedure allows 500–1000 or more syntheses to be conducted simultaneously. Houghten et al., supra, at 5134.

Preferred nucleic acid fragments of the present invention include nucleic acid molecules encoding epitope-bearing portions of the Ck beta-11 and/or LAI-1 protein.

The inventors have determined that the above polypeptide fragments are antigenic regions of the Ck beta-1 and/or LAI-1 protein. Methods for determining other such epitope-bearing portions of the Ck beta-11 and/or LAI- 1 protein are described in detail below.

Methods for determining other such epitope-bearing portions of an Ck beta-11 and/or LAI-1 polypeptide are described herein.

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985). Generally, animals can be immunized with free peptide; however, anti-peptide antibody titer can be boosted by coupling of the peptide to a macromolecular carrier, such as keyhole limpet hemacyanin (KLH) or tetanus toxoid. For instance, peptides containing cysteine can be coupled to carrier using a linker such as m-maleimidobenzoyl-N-hydroxysuccinimide ester (MBS), while other peptides can be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 g peptide or carrier protein and Freund's adjuvant. Several booster injections can be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal can be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein can be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, Ck beta-11 and/or LAI-1 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g. for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric Ck beta-11 and/or LAI-1 protein or protein fragment alone (Fountoulakis et al., *J. Biochem* 270:3958–3964 (1995)).

Polypeptide Purification and Isolation. LAI-1 and/or Ck beta-11 are recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention can be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention can be glycosylated with mammalian or other eukaryotic carbohydrates or can be non-glycosylated. Polypeptides of the invention can also include an initial methionine amino acid residue.

Antibodies. Ck beta-11 and/or LAI-1-protein specific antibodies for use in the present invention can be raised against the intact Ck beta-11 and/or LAI-1 protein or an antigenic polypeptide fragment thereof, which can presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to Ck beta-11 and/or LAI-1 protein. Fab and F(ab')$_2$ fragments lack the Fc fragment of intact antibody, clear more rapidly from the circulation, and can have less non-specific tissue binding of an intact antibody (Wahl et al., *J. Nucl. Med.* 24:316–325 (1983)). Thus, these fragments are preferred.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain and humanized antibodies, as well as Fab fragments, or the product of an Fab expression library. Various procedures known in the art can be used for the production of such antibodies and fragments.

Antibodies generated against the polypeptides corresponding to a sequence of the present invention or its in vivo receptor can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptides from tissue expressing that polypeptide.

For preparation of monoclonal antibodies, any technique which provides antibodies produced by continuous cell line cultures can be used. Examples include the hybridoma technique (Kohler and Milstein, 1975, *Nature*, 256:495–497), the trioma technique, the human B-cell hybridoma technique (Kozbor et al., 1983, *Immunology Today* 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptides products of this invention.

The antibodies of the present invention can be prepared by any of a variety of methods. For example, cells expressing the Ck beta-11 and/or LAI-1 protein or an antigenic fragment thereof can be administered to an animal in order to induce the production of sera containing polyclonal antibodies. In a preferred method, a preparation of Ck beta-11 and/or LAI-1 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or Ck beta-11 and/or LAI-1 protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J Immunol.* 6:292 (1976); Hammerling et al., In: *Monoclonal Antibodies and T-Cell Hybridomas,* Elsevier, N.Y., (1981) pp. 563–681 ). In general, such procedures involve immunizing an animal (preferably a mouse) with an Ck beta-11 and/or LAI-1 protein antigen or, more preferably, with an Ck beta-11 and/or LAI-1 protein-expressing cell. Suitable cells can be recognized by their capacity to bind anti-Ck beta-11 and/or LAI-1 protein antibody. Such cells can be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 g/ml of streptomycin. The splenocytes of such mice are extracted and fused with a suitable myeloma cell line. Any suitable myeloma cell line can be employed in accordance with the present invention; however, it is preferable to employ the parent myeloma cell line (SP20), available from the American Type Culture Collection, Rockville, Maryland. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the Ck beta-11 and/or LAI-1 protein antigen.

Alternatively, additional antibodies capable of binding to the Ck beta-11 and/or LAI-1 protein antigen can be produced in a two-step procedure through the use of anti-idiotypic antibodies. Such a method makes use of the fact that antibodies are themselves antigens, and that, therefore, it is possible to obtain an antibody which binds to a second antibody. In accordance with this method, Ck beta-11 and/or LAI-1-protein specific antibodies are used to immunize an animal, preferably a mouse. The splenocytes of such an animal are then used to produce hybridoma cells, and the hybridoma cells are screened to identify clones which produce an antibody whose ability to bind to the Ck beta-11 and/or LAI-1 protein-specific antibody can be blocked by the Ck beta-11 and/or LAI-1 protein antigen. Such antibodies comprise anti-idiotypic antibodies to the Ck beta-11 and/or LAI-1 protein-specific antibody and can be used to immunize an animal to induce formation of further Ck beta-11 and/or LAI-1 protein-specific antibodies.

It will be appreciated that Fab and F(ab')$_2$ and other fragments of the antibodies of the present invention can be used according to the methods disclosed herein. Such fragments are typically produced by proteolytic cleavage, using enzymes such as papain (to produce Fab fragments) or pepsin (to produce F(ab')$_2$ fragments). Alternatively, Ck beta-11 and/or LAI-1 protein-binding fragments can be produced through the application of recombinant DNA technology or through synthetic chemistry.

It can be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the Ck beta-11 and/or LAI-1 protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the 125I or 131I-labeled monoclonal antibody by the liver. In addition, this radionucleotide has a more favorable gamma emission energy for imaging (Perkins et al., *Eur. J Nucl. Med.* 10:296–301 (1985); Carasquillo et al., *J. Nucl. Med.* 28:281–287 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1–31 (1976), and Schurs et al., *Clin. Chim. Acta* 81:1–40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Chromosome Assays. The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an Ck beta-11 and/or LAI-1 protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error can be necessary to identify a genomic probe that gives a good in situ hybridization signal.

Briefly, sequences can be mapped to chromosomes by preparing PCR primers (preferably 15-25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man,* available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting LAI-1 and/or Ck beta-11 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the polypeptides of the present invention, is used to design an antisense RNA oligonucleotide of from about 10 to 40 base pairs in length. A DNA oligonucleotide is designed to be complementary to a region of the gene involved in transcription (triple helix see Lee et al., Nucl. Acids Res., 6:3073 (1979); Cooney et al, Science, 241:456 (1988); and Dervan et al., Science, 251: 1360 (1991)), thereby preventing transcription and the production of LAI-1 and/or Ck beta-11. The antisense RNA oligonucleotide hybridizes to the mRNA in vivo and blocks translation of the mRNA molecule into the LAI-1 and/or Ck beta-11 (antisense - Okano, J. Neurochem., 56:560 (1991); Oligodeoxynucleotides as Antisense Inhibitors of Gene Expression, CRC Press, Boca Raton, Fla. (1988)).

Alternatively, the oligonucleotides described above can be delivered to cells by procedures in the art such that the antisense RNA or DNA can be expressed in vivo to inhibit production of LAI-1 and/or Ck beta-11 in the manner described above.

Accordingly, antisense constructs to the LAI-1 and/or Ck beta-11 can be used to treat disorders which are either Ck beta-11 and/or LAI-1-induced or enhanced, for example, atherosclerosis, auto-immune, e.g. multiple sclerosis and insulin-dependent diabetes, and chronic inflammatory and infective diseases, histamine-mediated allergic reactions, rheumatoid arthritis, silicosis, sarcoidosis, idiopathic pulmonary fibrosis and other chronic inflammatory diseases of the lung, idiopathic hyper-eosinophilic syndrome, endotoxic shock, histamine-mediated allergic reactions, prostaglandin-independent fever, and aplastic anemia and other cases of bone marrow failure.

Antagonists, Agonists, Polypeptides and Methods. This invention further provides methods for screening compounds to identify agonists and antagonists to the chemokine polypeptides of the present invention. An agonist is a compound which has similar biological functions, or enhances the functions, of the polypeptides, while antagonists block such functions. Chemotaxis can be assayed by placing cells, which are chemoattracted by either of the polypeptides of the present invention, on top of a filter with pores of sufficient diameter to admit the cells (about 5 $\mu$m). Solutions of potential agonists, antagonists or polypeptides are placed in the bottom of the chamber with an appropriate control medium in the upper compartment, and thus a concentration gradient of the agonist, antagonist or polypeptides is measured by counting cells that migrate into or through the porous membrane over time.

Alternatively, a mammalian cell or membrane preparation expressing the receptors of the polypeptides would be incubated with a labeled chemokine polypeptide, e.g. radioactivity, in the presence of the compound. The ability of the compound to block this interaction could then be measured. When assaying for agonists in this fashion, the chemokines would be absent and the ability of the agonist itself to interact with the receptor could be measured.

Examples of potential LAI-1 and/or Ck beta-11 antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple-helix, see Lee et al., *Nucl. Acids Res.* 6:3073 (1979); Cooney et al, *Science* 241:456 (1988); and Dervan et al., *Science* 251:1360 (1991)), thereby preventing transcription and the production of the chemokine polypeptides. The antisense RNA oligonucleotide hybridizes to the mRNA in vivo and blocks translation of the mRNA molecule into the polypeptides (antisense—Okano, *J. Neurochem.* 56:560 (1991); oligodeoxynucleotides as Antisense Inhibitors of Gene Expression, CRC Press, Boca Raton, Fla. (1988)). The oligonucleotides described above can also be delivered to cells such that the antisense RNA or DNA can be expressed in vivo to inhibit production of the chemokine polypeptides.

Another potential chemokine antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

Another potential human chemokine antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists may be employed to inhibit the chemotaxis and activation of macrophages and their precursors, and of neutrophils, basophils, B lymphocytes and some T cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes.

The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the human chemokine polypeptides of the present invention.

The antagonists may also be employed for treating atherosclerosis, by preventing monocyte infiltration in the artery wall.

The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated.

The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung.

Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies.

The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines.

The antagonists may also be employed to treat cases of bone marrow failure, for example, aplastic anemia and myelodysplastic syndrome.

The antagonists may also be employed to treat asthma and allergy by preventing eosinophil accumulation in the lung. The antagonists may also be employed to treat subepithelial basement membrane fibrosis which is a prominent feature of the asthmatic lung.

The antagonists may be employed in a composition with a pharmaceutically acceptable carrier, e.g., as hereinafter described.

The antagonists can be employed to treat disorders which are either Ck beta-11 and/or LAI-1-induced or enhanced, for example, auto-immune and chronic inflammatory and infectious diseases. Examples of auto-immune diseases include multiple sclerosis, and insulin-dependent diabetes.

The antagonists can also be employed to treat infectious diseases including silicosis, sarcoidosis, idiopathic pulmonary fibrosis by preventing the recruitment and activation of mononuclear phagocytes. They can also be employed to treat idiopathic hyper-eosinophilic syndrome by preventing eosinophil production and migration. Endotoxic shock can also be treated by the antagonists by preventing the migration of macrophages and their production of the chemokine polypeptides of the present invention.

The antagonists can also be employed for treating atherosclerosis, by preventing monocyte infiltration in the artery wall.

The antagonists can also be employed to treat histamine mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema can also be treated.

The antagonists can also be employed to treat chronic and acute inflammation by preventing the attraction of monocytes to a wound area. They can also be employed to regulate normal pulmonary macrophage populations, since chronic and acute inflammatory pulmonary diseases are associated with sequestration of mononuclear phagocytes in the lung.

Antagonists can also be employed to treat rheumatoid arthritis by preventing the attraction of monocytes into synovial fluid in the joints of patients. Monocyte influx and activation plays a significant role in the pathogenesis of both degenerative and inflammatory arthropathies.

The antagonists, agonists or polypeptides can be employed to interfere with the deleterious cascades attributed primarily to IL-1 and TNF, which prevents the biosynthesis of other inflammatory cytokines. In this way, the antagonists, agonists or polypeptides can be employed to prevent inflammation. The antagonists can also be employed to inhibit prostaglandin-independent fever induced by chemokines.

The antagonists can also be employed to treat cases of bone marrow failure, for example, aplastic anemia and myelodysplastic syndrome.

The antagonists can also be employed to treat asthma and allergy by preventing eosinophil accumulation in the lung. The antagonists can also be employed to treat subepithelial basement membrane fibrosis which is a prominent feature of the asthmatic lung.

Agonists. LAI-1 and Ck beta-11 agonists include any small molecule that has an activity similar to any one or more of these polypeptides, as described herein. For example, Ck beta-11 agonists can be used to enhance Ck beta-11 activity. For example, to enhance Ck beta-11 induced myeloprotection in patients undergoing chemotherapy or bone marrow transplantation. As another example, LAI-1 agonists can provide one or more of anti-inflammatory activity, anti-TNFα activity, anti-cancer activity, antiangiogenic activity, and the like, as described herein for various functional activities of LAI-1.

Disease Diagnosis and Prognosis. Certain diseases or disorders, as discussed below, can be associated with enhanced levels of the Ck beta-11 and/or LAI-1 protein and mRNA encoding the Ck beta-11 and/or LAI-1 protein when compared to a corresponding "standard" mammal, i.e., a mammal of the same species not having the disease or disorder. Further, it is believed that enhanced levels of the Ck beta-11 and/or LAI-1 protein can be detected in certain body fluids (e.g. sera, plasma, urine, and spinal fluid) from mammals with a disease or disorder when compared to sera from mammals of the same species not having the disease or disorder. Thus, the invention provides a diagnostic method, which involves assaying the expression level of the gene encoding the Ck beta-11 and/or LAI-1 protein in mammalian cells or body fluid and comparing the gene expression level with a standard Ck beta-11 and/or LAI-1 gene expression level, whereby an increase in the gene expression level over the standard is indicative of certain diseases or disorders.

Where a disease or disorder diagnosis has already been made according to conventional methods, the present invention is useful as a prognostic indicator, whereby patients exhibiting enhanced Ck beta-11 and/or LAI-1 gene expression will experience a worse clinical outcome relative to patients expressing the gene at a lower level.

By "assaying the expression level of the gene encoding the Ck beta-11 and/or LAI-1 protein" is intended qualitatively or quantitatively measuring or estimating the level of the Ck beta-11 and/or LAI-1 protein or the level of the mRNA encoding the Ck beta-11 and/or LAI-1 protein in a first biological sample either directly (e.g. by determining or estimating absolute protein level or mRNA level) or relatively (e.g. by comparing to the Ck beta-11 and/or LAI-1 protein level or mRNA level in a second biological sample).

Preferably, the Ck beta-11 and/or LAI-1 protein level or mRNA level in the first biological sample is measured or estimated and compared to a standard Ck beta-11 and/or LAI-1 protein level or mRNA level, the standard being taken from a second biological sample obtained from an individual not having the disease or disorder. As will be appreciated in the art, once a standard Ck beta-11 and/or LAI-1 protein level or mRNA level is known, it can be used repeatedly as a standard for comparison.

By "biological sample" is intended any biological sample obtained from an individual, cell line, tissue culture, or other source which contains Ck beta-11 and/or LAI-1 protein or mRNA. Biological samples include mammalian body fluids (such as sera, plasma, urine, synovial fluid and spinal fluid) which contain secreted mature Ck beta-11 and/or LAI-1 protein, and ovarian, prostate, heart, placenta, pancreas, ascites, muscle, skin, glandular, kidney, liver, spleen, lung, bone, bone marrow, ocular, peripheral nervous, central nervous, breast and umbilical tissue. Methods for obtaining tissue biopsies and body fluids from mammals are well known in the art. Where the biological sample is to include mRNA, a tissue biopsy is the preferred source.

The present invention is useful for detecting disease in mammals. In particular the invention is useful during useful for diagnosis or treatment of various immune system-related disorders in mammals, preferably humans. Such disorders include tumors, cancers, and any disregulation of immune cell function including, but not limited to, autoimmunity, arthritis, leukemias, lymphomas, immunosuppression, sepsis, wound healing, acute and chronic infection, cell mediated immunity, humoral immunity, inflammatory bowel disease, myelosuppression, and the like. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the Ck beta-11 and/or LAI-1 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Ck beta-11 and/or LAI-1 protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the Ck beta-11 and/or LAI-1 protein). Northern blot analysis can be performed as described above.

Preferably, levels of mRNA encoding the Ck beta-11 and/or LAI-1 protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the Ck beta-11 and/or LAI-1 protein)) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying Ck beta-11 and/or LAI-1 protein levels in a biological sample can occur using any art-known method. Preferred for assaying Ck beta-11 and/or LAI-1 protein levels in a biological sample are antibody-based techniques. For example, Ck beta-11 and/or LAI-1 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g. with urea and neutral detergent, for the liberation of Ck beta-11 and/or LAI-1 protein for Western-blot or dot/slot assay (Jalkanen, M., et al., *J. Cell. Biol.* 101:976–985 (1985); Jalkanen, M., et al., *J. Cell. Biol* 105.3087–3096 (1987)). In this technique, which is based on the use of cationic solid phases, quantitation of Ck beta-11 and/or LAI-1 protein can be accomplished using isolated Ck beta-11 and/or LAI-1 protein as a standard. This technique can also be applied to body fluids. With these samples, a molar concentration of Ck beta-11 and/or LAI-1 protein will aid to set standard values of Ck beta-11 and/or LAI-1 protein content for different body fluids, like serum, plasma, urine, spinal fluid, etc. The normal appearance of Ck beta-11 and/or LAI-1 protein amounts can then be set using values from healthy individuals, which can be compared to those obtained from a test subject.

Other antibody-based methods useful for detecting Ck beta-11 and/or LAI-1 protein gene expression include immunoassays, such as the enzyme linked immunosorbent assay (ELISA) and the radioimmunoassay (RIA). For example, an Ck beta-11 and/or LAI-1 protein-specific monoclonal antibodies can be used both as an immunoabsorbent and as an enzyme-labeled probe to detect and quantify the Ck beta-11 and/or LAI-1 protein. The amount of Ck beta-11 and/or LAI-1 protein present in the sample can be calculated by reference to the amount present in a standard preparation using a linear regression computer algorithm. In another ELISA assay, two distinct specific monoclonal antibodies can be used to detect Ck beta-11 and/or LAI-1 protein in a body fluid. In this assay, one of the antibodies is used as the immunoabsorbent and the other as the enzyme-labeled probe.

The above techniques can be conducted essentially as a "one-step" or "two-step" assay. The "one-step" assay involves contacting Ck beta-11 and/or LAI-1 protein with immobilized antibody and, without washing, contacting the mixture with the labeled antibody. The "two-step" assay involves washing before contacting the mixture with the labeled antibody. Other conventional methods can also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label can be assayed by measuring the concentration of hydrogen peroxide formed by the enzyme-labelled antibody/substrate reaction. Besides enzymes, other suitable labels include radioisotopes, such as iodine ($^{125}I$, $^{121}I$), carbon ($^{14}C$), sulphur ($^{35}S$), tritium ($^{3}H$), indium ($^{112}In$), and technetium ($^{99m}Tc$), and fluorescent labels, such as fluorescein and rhodamine, and biotin.

The polypeptides of the present invention, and polynucleotides encoding such polypeptides, can be employed as research reagents for in vitro purposes related to scientific research, synthesis of DNA and manufacture of DNA vectors, and for the purpose of developing therapeutics and diagnostics for the treatment of human disease. For example, LAI-1 and Ck beta-11 can be employed for the expansion of immature hematopoietic progenitor cells, for example, granulocytes, macrophages or monocytes, by temporarily preventing their differentiation. These bone marrow cells can be cultured in vitro.

Fragments of the full length LAI-1 and/or Ck beta-11 genes can be used as a hybridization probe for a cDNA library to isolate the full length gene and to isolate other genes which have a high sequence similarity to the gene or similar biological activity. Preferably, however, the probes have at least 30 bases and can contain, for example, 50 or more bases. The probe can also be used to identify a cDNA clone corresponding to a full length transcript and a genomic clone or clones that contain the complete genes including regulatory and promotor regions, exons, and introns. An example of a screen comprises isolating the coding region of the genes by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

This invention is also related to the use of the LAI-1 and/or Ck beta-11 gene as part of a diagnostic assay for detecting diseases or susceptibility to diseases related to the presence of mutations in the nucleic acid sequences. Such diseases are related to under-expression of the chemokine polypeptides.

Individuals carrying mutations in the LAI-1 and/or Ck beta-11 can be detected at the DNA level by a variety of techniques. Nucleic acids for diagnosis can be obtained from a patient's cells, such as from blood, urine, saliva, tissue biopsy and autopsy material. The genomic DNA can be used directly for detection or can be amplified enzymatically by using PCR (Saiki et al., *Nature* 324:163–166(1986)) prior to analysis. RNA or cDNA can also be used for the same purpose. As an example, PCR primers complementary to the nucleic acid encoding LAI-1 and/or Ck beta-11 can be used to identify and analyze LAI-1 and/or Ck beta-11 mutations. For example, deletions and insertions can be detected by a change in size of the amplified product in comparison to the normal genotype. Point mutations can be identified by hybridizing amplified DNA to radiolabeled LAI-1 and/or Ck beta-11 RNA or alternatively, radiolabeled LAI-1 and/or Ck beta-11 antisense DNA sequences. Perfectly matched sequences can be distinguished from mismatched duplexes by RNase A digestion or by differences in melting temperatures.

Genetic testing based on DNA sequence differences can be achieved by detection of alteration in electrophoretic mobility of DNA fragments in gels with or without denaturing agents. Small sequence deletions and insertions can be visualized by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g. Myers et al., *Science* 230:1242 (1985)).

Sequence changes at specific locations can also be revealed by nuclease protection assays, such as RNase and S1 protection or the chemical cleavage method (e.g. Cotton et al., *PNAS, USA* 85:4397–4401 (1985)).

Thus, the detection of a specific DNA sequence can be achieved by methods such as hybridization, RNase protection, chemical cleavage, direct DNA sequencing or the use of restriction enzymes, (e.g. Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of LAI-1 and/or Ck beta-11 protein in various tissues since an over-expression of the proteins compared to normal control tissue samples can detect the presence of a disease or susceptibility to a disease, for example, a tumor. Assays used to detect levels of LAI-1 and/or Ck beta-11 protein in a sample derived from a host are well-known to those of skill in the art and include radioimmunoassays, competitive-binding assays, Western Blot analysis, ELISA assays and "sandwich" assay. An ELISA assay (Coligan, et al., *Current Protocols in Immunology* 1(2), Chapter 6, (1991)) initially comprises preparing an antibody specific to the Ck beta-11 and LAI-1 antigens, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any LAI-1 and/or Ck beta-11 proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to LAI-1 and/or Ck beta-11. Unattached reporter antibody is then washed out. Peroxidase substrates are then added to the dish and the amount of color developed in a given time period is a measurement of the amount of LAI-1 and/or Ck beta-11 protein present in a given volume of patient sample when compared against a standard curve.

A competition assay can be employed wherein antibodies specific to LAI-1 and/or Ck beta-11 are attached to a solid support and labeled Ck beta-11, MIP-4 and LAI-1 and a sample derived from the host are passed over the solid support and the amount of label detected, for example by liquid scintillation chromatography, can be correlated to a quantity of protein in the sample.

A "sandwich" assay is similar to an ELISA assay. In a "sandwich" assay LAI-1 and/or Ck beta-11 is passed over a solid support and binds to antibody attached to a solid support. A second antibody is then bound to the LAI-1 and/or Ck beta-11. A third antibody which is labeled and specific to the second antibody is then passed over the solid support and binds to the second antibody and an amount can then be quantified.

This invention provides a method for identification of the receptors for the chemokine polypeptides. The gene encoding the receptor can be identified by numerous methods known to those of skill in the art, for example, ligand panning and FACS sorting (Coligan, el al., *Current Protocols in Immun.* 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Therapeutics. Polypeptides of the present invention can be used in a variety of immunoregulatory and inflammatory functions and also in a number of disease conditions. LAI-1 and/or Ck beta-11 are in the chemokine family and therefore they are a chemo-attractant for leukocytes (such as monocytes, neutrophils, T lymphocytes, eosinophils, basophils, etc.).

Northern Blot analyses show that LAI-1 and/or Ck beta-11 are expressed predominantly is tissues of hemopoietic origin.

The human chemokine polypeptides may be employed to inhibit bone marrow stem cell colony formation as adjunct protective treatment during cancer chemotherapy and for leukemia.

The human chemokine polypeptides may also be employed to inhibit epidermal keratinocyte proliferation for treatment of psoriasis, which is characterized by keratinocyte hyper-proliferation.

The human chemokine polypeptides may also be employed to treat solid tumors by stimulating the invasion and activation of host defense cells, e.g., cytotoxic T cells and macrophages and by inhibiting the angiogenesis of tumors. They may also be employed to enhance host defenses against resistant chronic and acute infections, for example, mycobacterial infections via the attraction and activation of microbicidal leukocytes.

The human chemokine polypeptides may also be employed to inhibit T cell proliferation by the inhibition of IL-2 biosynthesis for the treatment of T-cell mediated autoimmune diseases and lymphocytic leukemias.

They may also be employed to regulate hematopoiesis, by regulating the activation and differentiation of various hematopoietic progenitor cells, for example, to release mature leukocytes from the bone marrow following chemotherapy.

Ck beta-11 Therapeutic/Diagnostic Applications. Ck beta-11 is shown to play an important role in the regulation of the immune response and inflammation. Accordingly, administration of Ck beta-11 is employed to stimulate or regulate the immune response of a host. Ck beta-11 could be used as an anti-inflammatory agent.

As illustrated in FIG. 3 and Example 8, there is some chemoattractant activity attributable to Ck beta-11.

Further, the polypeptides of the present invention can be useful in anti-tumor therapy since there is evidence that chemokine expressing cells injected into tumors have caused regression of the tumor, for example, in the treatment of Karposi sarcoma. Ck beta-11 can induce cells to secrete TNF-α, which is a known agent for regressing tumors, in which case this protein could be used to induce tumor regression. Ck beta-11 can also induce human monocytes to secrete other tumor and cancer inhibiting agents such as IL-6, IL-1 and G-CSF. Also, LAI-1 and/or Ck beta-11 stimulate the invasion and activation of host defense (tumoricidal) cells, e.g. cytotoxic T-cells and macrophages via their chemotactic activity, and in this way can also be used to treat solid tumors.

The polypeptides can also be employed to inhibit the proliferation and differentiation of hematopoietic cells and therefore can be employed to protect bone marrow stem cells from chemotherapeutic agents during chemotherapy.

The inhibitory effect of the LAI-1 and Ck beta-11 polypeptides on the subpopulation of committed progenitor cells, (for example granulocyte, and macrophage/monocyte cells) can be employed therapeutically to inhibit proliferation of leukemic cells.

The pharmaceutical compositions of the present invention are also useful in the treatment of leukemia, which causes a hyperproliferative myeloid cell state. Thus, the invention further provides methods for treating leukemia, which involve administering to a leukemia patient an effective amount of Ck beta-11 either alone or together with one or more chemokines selected from the group consisting of MIP-1α, MIP-2α, PF4, IL-8, MCAF, and MRP-2.

Certain chemokines, such as MIP-1β, MIP-2β and GRO-α, inhibit (at least partially block) the myeloid suppressive affects of the myelosuppresive compositions of the present invention. Thus, in a further embodiment, the invention provides methods for inhibiting myelosuppression, which involves administering an effective amount of a myelosuppressive inhibitor selected from the group consisting of MIP-1β, MIP-2β and GRO-α to a mammal previously exposed to the myelosuppresive agent Ck beta-11 either alone or together with one or more of MIP-1α, MIP-2α, PF4, IL-8, MCAF, and MRP-2.

One of ordinary skill will appreciate that effective amounts of the Ck beta-11 polypeptides for treating an individual in need of an increased level of Ck beta-11 activity (including amounts of Ck beta-11 polypeptides effective for myelosuppression with or without myelosuppressive agents or myelosuppressive inhibitors) can be determined empirically for each condition where administration of Ck beta-11 is indicated. The polypeptide having Ck beta-11 activity my be administered in pharmaceutical compositions in combination with one or more pharmaceutically acceptable excipients.

Ck beta-11 can also be employed to treat leukemia and abnormally proliferating cells, for example tumor cells, by inducing apoptosis. Ck beta-11 induces apoptosis in a population of hematopoietic progenitor cells.

In addition, since Ck beta-11 has effects on T-lymphocytes as well as macrophages, Ck beta-11 can enhance the capacity of antigen presenting cells (APCs) to take up virus, bacteria or other foreign substances, process them and present them to the lymphocytes responsible for immune responses. Ck beta-11 can also modulate the interaction of APCs with T-lymphocytes and B-lymphocytes. Ck beta-11 can provide a costimulatory signal during antigen presentation which directs the responding cell to survive, proliferate, differentiate, secrete additional cytokines or soluble mediators, or selectively removes the responding cell by inducing apoptosis or other mechanisms of cell death. Since APCs have been shown to facilitate the transfer of HIV to CD4+T-lymphocytes, Ck beta-11 can also influence this ability and prevent infection of lymphocytes by HIV or other viruses mediated through APCs. This is also true for the initial infection of APCs, T-lymphocytes or other cell types by HIV, EBV, or any other such viruses.

In addition, recent demonstration that the MIP-1a receptor serves as a cofactor in facilitating the entry of HIV into human monocytes and T-lymphocytes raises an interesting possibility that Ck beta-11 or its variants might interfere with the process of HIV entry into the cells. Thus, Ck beta-11 can be useful as an antiviral agent for viruses and retroviruses whose entry is facilitated by the MIP-1 a receptor.

Ck beta-11 can act as an immune enhancement factor by stimulating the intrinsic activity of T-lymphocytes to fight bacterial and viral infection as well as other foreign bodies. Such activities are useful for the normal response to foreign antigens such as infection of allergies as well as immuno-responses to neoplastic or benign growth including both solid tumors and leukemias.

For these reasons the present invention is useful for diagnosis or treatment of various immune system-related disorders in mammals, preferably humans. Such disorders include tumors, cancers, and any disregulation of immune cell function including, but not limited to, autoimmunity, arthritis, leukemias, lymphomas, immunosuppression, sepsis, wound healing, acute and chronic infection, cell mediated immunity, humoral immunity, inflammatory bowel disease, myelosuppression, and the like.

LAI-1 Therapeutic/Diagnostic Applications. LAI-1 activity is useful for immune enhancement or suppression, myeloprotection, stem cell mobilization, acute and chronic inflammatory control and treatment of leukemia. In addition, since LAI-1 has effects on T-lymphocytes as well as macrophages, LAI-1 enhances the capacity is of antigen presenting cells (APCs) to take up virus, bacteria or other foreign substances, process them and present them to the lymphocytes responsible for immune responses. In addition, LAI-1 also modulates the interaction of APCs with T-lymphocytes and B-lymphocytes. For instance, LAI-1 provides a costimulation signal during antigen presentation which directs the responding cell to survive, proliferate, differentiate, secrete additional cytokines or soluble mediators, or selectively removes the responding cell by inducing apoptosis or other mechanisms of cell death. Since APCs have been shown to facilitate the transfer of HIV to CD4+T-lymphocytes LAI-1 also influences this ability and prevents infection of lymphocytes by HIV or other viruses mediated through APCs. This is also true for the initial infection of APCs, T-lymphocytes or other cell types by HIV, EBV, or any other such viruses.

In addition, since LAI-1 directly effects T-lymphocytes in vivo, LAI-1 acts as an immune enhancement factor by stimulating the intrinsic activity of T-lymphocytes to fight bacterial and viral infection as well as other foreign bodies. Such activities are useful for the normal response to foreign antigens such as infection of allergies as well as immunoresponses to neoplastic or benign growth including both solid tumors and leukemias.

For these reasons the present invention is useful for diagnosis or treatment of various immune system-related disorders in mammals, preferably humans. Such disorders include tumors, cancers, and any disregulation of immune cell function including, but not limited to, autoimmunity, arthritis, asthma, leukemias, lymphomas, immunosuppression, sepsis, wound healing, acute and chronic infection, cell mediated immunity, humoral immunity, inflammatory bowel disease, myelosuppression, and the like.

LAI-1, as an antiinflammatory, can treat such disorders as, but not limited to, those involving abnormal production of TNFα. Such disorders include, but are not limited to, sepsis syndrome, including cachexia, circulatory collapse and shock resulting from acute or chronic bacterial infection, acute and chronic parasitic or infectious processes, including bacterial, viral and fungal infections, acute and chronic immune and autoimmune pathologies, such as systemic lupus erythematosus and rheumatoid arthritis, alcohol-induced hepatitis, chronic inflammatory pathologies such as sarcoidosis and Crohn's pathology, vascular inflammatory pathologies such as disseminated intravascular coagulation, graft-versus-host pathology, Kawasaki's pathology; malignant pathologies involving TNF-secreting tumors and neurodegenerative diseases.

Neurodegenerative diseases include, but are not limited to, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supra-nucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi-system disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis Hallerrorden-Spatz disease; and Dementia pugilistica. One preferred neurodegenerative disease is multiple sclerosis.

See, e.g., Berkow et al, eds., The Merck Manual, 16th edition, Merck and Co., Rahway, N. J., 1992, which reference, and references cited therein, are entirely incorporated herein by reference.

Accordingly, LAI-1 and/or Ck beta-11 can be used to facilitate wound healing by controlling infiltration of target immune cells to the wound area. In a similar fashion, the polypeptides of the present invention can enhance host defenses against chronic infections, e.g mycobacterial, via the attraction and activation of microbicidal leukocytes.

The polypeptides of the present invention, and polynucleotides encoding such polypeptides, can be employed as research reagents for in vitro purposes related to scientific research, synthesis of DNA and manufacture of DNA vectors, and for the purpose of developing therapeutics and diagnostics for the treatment of human disease. For example, LAI-1 and Ck beta-11 can be employed for the expansion of immature hematopoietic progenitor cells, for example, granulocytes, macrophages or monocytes, by temporarily preventing their differentiation. These bone marrow cells can be cultured in vitro.

Another use of the polypeptides is the inhibition of T-cell proliferation via inhibition of IL-2 biosynthesis, for example, in auto-immune diseases and lymphocytic leukemia.

LAI-1 and/or Ck beta-11 can also be useful for inhibiting epidermal keratinocyte proliferation which has utility in psoriasis (keratinocyte hyper-proliferation) since Langerhans cells in skin have been found to produce MIP-1α.

LAI-1 and/or Ck beta-11 can be used to prevent scarring during wound healing both via the recruitment of debris-cleaning and connective tissue-promoting inflammatory cells and by its control of excessive TGFβ-mediated fibrosis, in addition these polypeptides can be used to treat stroke, thrombocytosis, pulmonary emboli and myeloproliferative disorders, since LAI-1 and/or Ck beta-11 increase vascular permeability.

Pharmaceutical Compositions. The Ck beta-11 and/or LAI-1 polypeptide pharmaceutical composition comprises an effective amount of an isolated Ck beta-11 and/or LAI-1 polypeptide of the invention, particularly a mature form of the Ck beta-11 and/or LAI-1, effective to increase the Ck beta-11 and/or LAI-1 activity level in such an individual. Such compositions can be formulated and dosed in a fashion consistent with good medical practice, taking into account the clinical condition of the individual patient (especially the side effects of treatment with Ck beta-11 and/or LAI-1 polypeptide alone), the site of delivery of the Ck beta-11 and/or LAI-1 polypeptide composition, the method of administration, the scheduling of administration, and other factors known to practitioners. The "effective amount" of Ck beta-11 and/or LAI-1 polypeptide for purposes herein is thus determined by such considerations.

Polypeptides, antagonists or agonists of the present invention can be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The human chemokine polypeptides and agonists and antagonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and agonists and antagonists may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in the amount which is effective for treating and/or prophylaxis of the specific indication. In general, the polypeptides will be administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The Ck beta-11 and/or LAI-1 polypeptide is also suitably administered by sustained-release systems. Suitable examples of sustained-release compositions include semipermeable polymer matrices in the form of shaped articles, e.g. films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2- hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988). Sustained-release Ck beta-11 and/or LAI-1 polypeptide compositions also include liposomally entrapped Ck beta-11 and/or LAI-1 polypeptide. Liposomes containing Ck beta-11 and/or LAI-1 polypeptide are prepared by methods knownper se: DE 3,218,121; Epstein et al., *Proc. Natl. Acad Sci.* (*USA*) 82:3688–3692 (1985); Hwang et al., *Proc. Natl. Acad Sci.* (*USA*) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Ck beta-11 and/or LAI-1 polypeptide therapy.

For parenteral administration, in one embodiment, the Ck beta-11 and/or LAI-1 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the Ck beta-11 and/or LAI-1 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g. polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Ck beta-11 and/or LAI-1 polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of Ck beta-11 and/or LAI-1 polypeptide salts.

Ck beta-11 and/or LAI-1 polypeptide to be used for therapeutic administration must be sterile. Sterility is readily accomplished by filtration through sterile filtration membranes (e.g 0.2 micron membranes). Therapeutic Ck beta-1 and/or LAI-1 polypeptide compositions generally are placed into a container having a sterile access port, for example, an intravenous solution bag or vial having a stopper pierceable by a hypodermic injection needle. Ck beta-11 and/or LAI-1 polypeptide ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous Ck beta-11 and/or LAI-1 polypeptide solution, and the resulting mixture is lyophilized. The infusion solution is prepared by reconstituting the lyophilized Ck beta-11 and/or LAI-1 polypeptide using bacteriostatic Water-for-Injection. The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention can be employed in conjunction with other therapeutic compounds. Modes of administration. It will be appreciated that conditions caused by a decrease in the standard or normal level of Ck beta-11 and/or LAI-1 activity in an individual, can be treated by administration of Ck beta-11 and/or LAI-1 protein.

Thus, the invention further provides a method of treating an individual in need of an increased level of Ck beta-11 and/or LAI-1 activity comprising administering to such an individual a pharmaceutical composition comprising an effective amount of an isolated Ck beta-11 and/or LAI-1 polypeptide of the invention, particularly a mature form of the Ck beta-11 and/or LAI-1, effective to increase the Ck beta-11 and/or LAI-1 activity level in such an individual.

The amounts and dosage regimens of LAI-1 and/or Ck beta-11 administered to a subject will depend on a number of factors such as the mode of administration, the nature of the condition being treated and the judgment of the prescribing physician. The pharmaceutical compositions are administered in an amount which is effective for treating and/or prophylaxis of the specific indication. In general, the polypeptides will be administered in an amount of at least about 10 $\mu$tg/kg body weight and in most cases they will be administered in an amount not in excess of about 10 mg/kg body weight per day and preferably the dosage is from about 10 $\mu$g/kg body weight daily, taking into account the routes of administration, symptoms, etc.

As a general proposition, the total pharmaceutically effective amount of Ck beta-11 and/or LAI-1 polypeptide administered parenterally per dose will more preferably be in the range of about 1 $\mu$g/kg/day to 10 mg/kg/day of patient body weight, although, as noted above, this will be subject to therapeutic discretion. Even more preferably, this dose is at least 0.01 mg/kg/day, and most preferably for humans between about 0.01 and 1 mg/kg/day. If given continuously, the Ck beta-11 and/or LAI-1 polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution can also be employed. The length of treatment needed to observe changes and the interval following treatment for responses to occur appears to vary depending on the desired effect.

Pharmaceutical compositions containing the Ck beta-11 and/or LAI-1 of the invention can be administered orally, rectally, parenterally, intracistemally, intravaginally, intraperitoneally, topically (as by powders, ointments, drops or transdermal patch), bucally, or as an oral or nasal spray.

Gene Therapy. The chemokine polypeptides, and agonists or antagonists which are polypeptides, can be employed in accordance with the present invention by expression of such polypeptides in vivo, which is often referred to as "gene therapy." Thus, for example, cells from a patient can be engineered with a polynucleotide (DNA or RNA) encoding a polypeptide ex vivo, with the engineered cells then being provided to a patient to be treated with the polypeptides. Such methods are well-known in the art. For example, cells can be engineered by procedures known in the art by use of a retroviral particle containing RNA encoding the polypeptides of the present invention.

Similarly, cells can be engineered in vivo for expression of a polypeptide in vivo by, for example, procedures known in the art. As known in the art, a producer cell for producing a retroviral particle containing RNA encoding the polypeptides of the present invention can be administered to a patient for engineering the cells in vivo and expression of the polypeptides in vivo. These and other methods for administering polypeptides of the present invention by such method should be apparent to those skilled in the art from the teachings of the present invention. For example, the expression vehicle for engineering cells can be other than a retrovirus, for example, an adenovirus which can be used to engineer cells in vivo after combination with a suitable delivery vehicle.

The retroviral plasmid vectors can be derived from retroviruses which include, but are not limited to, Moloney Murine Sarcoma Virus, Moloney Murine Leukemia Virus, spleen necrosis virus, Rous Sarcoma Virus and Harvey Sarcoma Virus.

In a preferred embodiment the retroviral expression vector, pMV-7, is flanked by the long terminal repeats (LTRs) of the Moloney murine sarcoma virus and contains the selectable drug resistance gene neo under the regulation of the herpes simplex virus (HSV) thymidine kinase (tk) promoter. Unique EcoRI and HinduII sites facilitate the introduction of coding sequence (Kirschmeier, P. T. et al, *DNA* 7:219–25 (1988)).

The vectors include one or more suitable promoters which include, but are not limited to, the retroviral LTR; the SV40 promoter; and the human cytomegalovirus (CMV) promoter described in Miller, et al., *Biotechniques, Vol.* 7, No. 9:980–990 (1989), or any other promoter (e.g. cellular promoters such as eukaryotic cellular promoters including, but not limited to, the histone, pol III, and β-actin promoters). The selection of a suitable promoter will be apparent to those skilled in the art from the teachings contained herein.

The nucleic acid sequence encoding the polypeptide of the present invention is under the control of a suitable promoter which includes, but is not limited to, viral thymidine kinase promoters, such as the Herpes Simplex thymidine kinase promoter; retroviral LTRs, the P-actin promoter, and the native promoter which controls the gene encoding the polypeptide.

The retroviral plasmid vector is employed to transduce packaging cell lines to form producer cell lines. Examples of packaging cells which can be transfected include, but are not limited to, the PE501, PA317 and GP+am12. The vector can transduce the packaging cells through any means known in the art. Such means include, but are not limited to, electroporation, the use of liposomes, and $CaPO_4$ precipitation.

The producer cell line generates infectious retroviral vector particles which include the nucleic acid sequence(s) encoding the polypeptides. Such retroviral vector particles then can be employed, to transduce eukaryotic cells, either in vitro or in vivo. The transduced eukaryotic cells will express the nucleic acid sequence(s) encoding the polypeptide. Eukaryotic cells which can be transduced, include but are not limited to, fibroblasts and endothelial cells.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described. "Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but can vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which can be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation can be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

Having now generally described the invention, the same will be more readily understood through reference to the following example which is provided by way of illustration, and is not intended to be limiting of the present invention.

EXAMPLE 1

Bacterial Expression and Purification of Ckβ-11

The DNA sequence encoding for Ckβ-11, ATCC # 75948, is initially amplified using PCR oligonucleotide primers corresponding to the 5' and 3' end sequences of the processed Ckβ-11 nucleic acid sequence (minus the putative signal peptide sequence). Additional nucleotides corresponding to the Ckβ-11 gene are added to the 5' and 3' end sequences respectively. The 5' oligonucleotide primer has the sequence 5° CCCGCATGCCAACTCTGAGTG-GCACCA 3' (SEQ ID NO:5) contains a SphI restriction enzyme site (bold) followed by 18 nucleotides of Ckβ-11 coding sequence (underlined) starting from the second nucleotide of the sequences coding for the mature protein. The ATG codon is included in the SphI site. In the next codon following the ATG, the first base is from the SphI site and the remaining two bases correspond to the second and third base of the first codon (residue 18) of the putative mature protein. The 3' sequence 5' CCCGGATCCCAAT-GCTTCGGACT 3' (SEQ ID NO:6) contains complementary sequences to a BamH1 site (bold) and is followed by 18 nucleotides of gene specific sequences preceding the termination codon. The restriction enzyme sites correspond to the restriction enzyme sites on the bacterial expression vector pQE-9 (Qiagen, Inc. Chatsworth, Calif.). pQE-9 encodes antibiotic resistance (Amp$^r$, a bacterial origin of replication (ori), an IPTG-regulatable promoter operator (P/O), a ribosome binding site (RBS), a 6-His tag and restriction enzyme sites. pQE-9 is then digested with SphI and BamH1. The amplified sequences are ligated into pQE-9 and are inserted in frame with the sequence encoding for the histidine tag and the RBS. The ligation mixture is then used to transform the E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacd repressor and also confers kanamycin resistance (Kanr). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 μg/ml) and Kan (25 μg/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacd repressor, clearing the P/O leading to increased gene expression. Cells are grown an extra 3 to 4 hours. Cells are then harvested by centrifugation. The cell pellet is solubilized in the chaotropic agent 6 Molar Guanidine HCl pH 5.0. After clarification, solubilized Ckβ-11 is purified from this solution by chromatography on a Nickel-Chelate column under conditions that allow for tight binding by proteins containing the 6-His tag (Hochuli, E. et al., J. Chromatography 411:177–184 (1984)). Ckβ-11 (>98% pure) is eluted from the column in 6M guanidine HCl. Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Nichelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate.

EXAMPLE 2

Bacterial Expression and Purification of LAI-1

The DNA sequence encoding for LAI-1, ATCC # 75947, is initially amplified using PCR oligonucleotide primers corresponding to the 5' and 3' end sequences of the processed Ckα-1 nucleic acid sequence (minus the putative signal peptide sequence). Additional nucleotides corresponding to LAI-1 are added to the 5' and 3' end sequences respectively. The 5' oligonucleotide primer has the sequence 5' CCCGCATGCCTTCTGGAGGTCTATTACACA 3' (SEQ ID NO:7) contains a SphI restriction enzyme site (bold) followed by 21 nucleotides of LAI-1 coding sequence starting from the second nucleotide of the sequences coding for the mature protein. The ATG codon is included in the SphI site. In the next codon following the ATG, the first base is from the SphI site and the remaining two bases correspond to the second and third base of the first codon (residue 23) of the putative mature protein. As a consequence, the first base in this codon is changed from G to C comparing with the original sequences, resulting in a Val to Leu substitution in the recombinant protein. The 3' sequence 5' CCCGGATC-CGGGAATCTTTCTCTTAAAC 3' (SEQ ID NO:8) contains complementary sequences to a BamH1 site (bold) and is followed by 19 nucleotides of gene specific sequences preceding the termination codon. The restriction enzyme sites correspond to the restriction enzyme sites on the bacterial expression vector pQE-9 (Qiagen, Inc. Chatsworth, Calif.). pQE-9 encodes antibiotic resistance (Ampr), a bacterial origin of replication (ori), an IPTG-regulatable promoter operator (P/O), a ribosome binding site (RBS), a 6-His tag and restriction enzyme sites. pQE-9 is then digested with SphI and BamH1. The amplified sequences are ligated into pQE-9 and are inserted in frame with the sequence encoding for the histidine tag and the RBS. The ligation mixture is then used to transform the *E. coli* M15/rep 4 (Qiagen, Inc.) by the procedure described in Sambrook, J. et al., *Molecular Cloning: A Laboratory Manual*, Cold Spring Laboratory Press, (1989). M15/rep4 contains multiple copies of the plasmid pREP4, which expresses the lacd repressor and also confers kanamycin resistance (KanD. Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 μg/ml) and Kan (25 μg/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the laci repressor, clearing the P/O leading to increased gene expression. Cells are grown an extra 3 to 4 hours. Cells are then harvested by centrifugation. The cell pellet is solubilized in the chaotropic agent 6 Molar Guanidine HCl pH 5.0. After clarification, solubilized LAI-1 is purified from this solution by chromatography on a Nickel Chelate column under conditions that allow for tight binding by proteins containing the 6-His tag (Hochuli, E. et al., *J. Chromatography* 411:177–184 (1984)). LAI-1 (>98% pure) is eluted from the column in 6M guanidine HCl. Protein renaturation out of GnHCl can be accomplished by several protocols (Jaenicke, R. & Rudolph, R., *Protein Structure A Practical Approach*, IRL Press, New York (1990)). Initially, step dialysis is utilized to remove the GnHCL. Alternatively, the purified protein isolated from the Nichelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containing 5 mM Ammonium Bicarbonate.

EXAMPLE 3

Expression of Recombinant Ckβ-11 in COS cells

The expression of plasmid, Ckβ-11HA is derived from a vector pcDNAI/Amp (Invitragen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire Ckβ-11 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, et al., *Cell* 37:767 (1984)). The infusion of HA tag to the target protein allows easy detection of the recombinant protein with an antibody that recognizes the HA epitope.

The plasmid construction strategy is described as follows:

The DNA sequence encoding for Ckβ-11, ATCC # 75948, is constructed by PCR using two primers: the 5' primer 5' AAAAAGCTTGCCATGGCCCTGCTACTG 3' (SEQ ID NO:9) contains a HindIII site followed by 18 nucleotides of Ckβ-11 coding sequence starting from the minus 3 position relative to initiation codon; the 3' sequence 5' CGCTCTA-GATTAAGCGTAGTCTGGGACGTCG-TATGGGTATAGGTTAACTGCTGCGAC 3' (SEQ ID NO: 10) contains complementary sequences to an XbaI site, translation stop codon, HA tag and the last 18 nucleotides of the Ckβ-11 coding sequence (not including the stop codon). Therefore, the PCR product contains a HindIII site, Ckβ-11 coding sequence followed by HA tag fused in frame, a translation termination stop codon next to the HA tag, and an XbaI site. The PCR amplified DNA fragment and the vector, pcDNAI/Amp, are digested with HindIII and XbaI restriction enzyme and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant Ckβ-11, COS cells are transfected with the expression vector by DEAEDEXTRAN method (J. Sambrook, et al., *Molecular Cloning: A Laboratory Manual*, Cold Spring Laboratory Press, (1989)). The expression of the Ckβ-11 HA protein is detected by radiolabelling and immunoprecipitation method (E. Harlow, & D. Lane, *Antibodies: A Laboratory Manual*, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed by SDS-PAGE.

EXAMPLE 4

Expression of Recombinant LAI-1 in COS cells

The expression of plasmid, LAI-1 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire LAI-1 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, et al., *Cell* 37:767 (1984)). The infusion of HA tag to the target protein allows easy detection of the recombinant protein with an antibody that recognizes the HA epitope.

The plasmid construction strategy is described as follows: The DNA sequence encoding for LAI-1, ATCC # 75947, is constructed by PCR using two primers: the 5' primer 5' AAAAAGCTTAGAATGAAGTTCATCTCG 3' (SEQ ID NO:1 1) contains a HindIII site followed by 18 nucleotides of LAI-1 coding sequence starting from the minus 3 position relative to the initiation codon; the 3' sequence 5° CGCTCTAGATTAAGCGTAGTCTGG-GACGTCGTATGGGTAG GGAATCTTTCTCTT 3' (SEQ ID NO: 12) contains complementary sequences to an XbaI site, translation stop codon, HA tag and the last 18 nucleotides of the LAI-1 coding sequence (not including the stop codon). Therefore, the PCR product contains a HindIII site, LAI-1 coding sequence followed by HA tag fused in frame, a translation termination stop codon next to the HA tag, and an XbaI site. The PCR amplified DNA fragment and the vector, PcDNAI/Amp, are digested with HindIII and an XbaI restriction enzyme and ligated. The ligation mixture is transformed into E. coli strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant LAI-1, COS cells are transfected with the expression vector by DEAE-DEXTRAN method (J. Sambrook, et al., *Molecular Cloning: A Laboratory Manual*, Cold Spring Laboratory Press, (1989)). The expression of the LAI-1 HA protein is detected by radiolabelling and immunoprecipitation method (E. Harlow, & D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed by SDS-PAGE.

EXAMPLE 5

Cloning and expression of Ckβ-11 using the baculovirus expression system

The DNA sequence encoding the full length Ckβ-11 protein, ATCC #75948, was amplified using PCR oligonucleotide primers corresponding to the 5' and 3' sequences of the gene:

The 5' primer has the sequence 5' CGCGGGATCCGC-CATCATG GCCCTGCTACTGGCCCT 3' (SEQ ID NO:13) and contains a BamHI restriction enzyme site (in bold) followed by 6 nucleotides resembling an efficient signal for the initiation of translation in eukaryotic cells (Kozak, M.,*J. Mol. Biol.* 196:947–950 (1987)) which is just behind the first 20 nucleotides of the Ckβ-11 gene (the initiation codon for translation "ATG" is underlined).

The 3' primer has the sequence 5' CGGCGGTACCTG-GCTGCACGGTCCATAGG 3' (SEQ ID NO: 14) and contains the cleavage site for the restriction endonuclease Asp781 and 19 nucleotides complementary to the 3' non-translated sequence of the Ckβ-11 gene. The amplified sequences were isolated from a 1% agarose gel using a commercially available kit ("Geneclean," BIO 101 Inc., La Jolla, Calif.). The fragment was then digested with the endonucleases BamHI and Asp781 and then purified again on a 1% agarose gel. This fragment was designated F2.

The vector pRG1 (modification of pVL941 vector, discussed below) was used for the expression of the Ckβ-11 protein using the baculovirus expression system (for review see: Summers, M. D. & Smith, G. E., *A Manual of Methods for Baculovirus Vectors and Insect Cell Culture Procedures*, Texas Agricultural Experimental Station Bulletin No. 1555 (1987)). This expression vector contains the strong polyhedrin promoter of the Autographa californica nuclear polyhedrosis virus (AcMNPV) followed by the recognition sites for the restriction endonucleases BamHI and Asp781. The polyadenylation site of the simian virus (SV)40 was used for efficient polyadenylation. For an easy selection of recombinant viruses the beta-galactosidase gene from E. coli was inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. & Summers, M. D., *Virology* 170:31–39).

The plasmid was digested with the restriction enzymes BamHI and Asp781 and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA has been designated V2.

Fragment F2 and the dephosphorylated plasmid V2 were ligated with T4 DNA ligase. *E. coli* HB101 cells are then transformed and bacteria identified that contained the plasmid (pBac-Ckβ-11) with the CKβ-11 gene using the enzymes BamHI and Asp781. The sequence of the cloned fragment was confirmed by DNA sequencing.

5 μg of the plasmid pBac-CKβ-11 was cotransfected with 1.0 μg of a commercially available linearized baculovirus ("BaculoGold™ baculovirus DNA", Pharmingen, San Diego, Calif.) using the lipofection method (Felgner et al., *Proc. Natl Acad. Sci. USA* 84:7413–7417 (1987)).

1 μg of BaculoGoldTM virus DNA and 5 μg of the plasmid pBac-CKβ-11 were mixed in a sterile well of a microliter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate is rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gall" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculovirus is used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-CKP-11 at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they are harvested by centrifugation and the labelled proteins visualized by SDS-PAGE and autoradiography.

Several batches were obtained. Batch B1 was not recorded. In batch B2, the N-terminus of the major product was determined to be Gly (22)-Thr (23)-Asn (24). . . . Similarly, in batch B3, about 95% of the protein was determined to have an N-terminus of Gly(22)- Thr(23)-Asn (24). . . .

EXAMPLE 6

Cloning and expression of LAI-1 using the baculovirus expression system

The DNA sequence encoding the full length LAI-1 protein, ATCC # 75947, was amplified using PCR oligonucleotide primers corresponding to the 5' and 3' sequences of the gene:

The 5' primer had the sequence 5' GCCGGATCCGC-CATC ATGAAGTTCATCTCGACATC 3' (SEQ ID NO: 15) and contained a BamHI restriction enzyme site (in bold) followed by 6 nucleotides resembling an efficient signal for the initiation of translation in eukaryotic cells (Kozak, M.,*J. Mol. Biol.* 196:947–950 (1987)) which was just behind the first 20 nucleotides of the LAI-1 gene (the initiation codon for translation "ATG" is underlined).

The 3' primer had the sequence 5' CGCGGGTACCGG TGTTCTTAGTGGAAA 3' (SEQ ID NO: 16) and contained the cleavage site for the restriction endonuclease Asp781 (in bold) and 17 nucleotides complementary to the 3' non-translated sequence of the LAI-1 gene. The amplified sequences were isolated from a 1% agarose gel using a commercially available kit ("Geneclean," BIO 101 Inc., La Jolla, Calif.). The fragment was then digested with the endonucleases BamHI and Asp781 and then purified again on a 1% agarose gel. This fragment was designated F2.

The vector pRGI (modification of pVL941 vector, discussed below) was used for the expression of the LAI-1 protein using the baculovirus expression system (for review see: Summers, M. D. & Smith, G. E., *A manual of methods for baculovirus vectors and insect cell culture procedures,* Texas Agricultural Experimental Station Bulletin No. 1555 (1987)). This expression vector contains the strong polyhedrin promoter of the Autographa californica nuclear polyhedrosis virus (AcMNPV) followed by the recognition sites for the restriction endonucleases BamHI and Asp781. The polyadenylation site of the simian virus (SV)40 was used for efficient polyadenylation. For an easy selection of recombinant viruses the beta-galactosidase gene from *E. coli* was inserted in the same orientation as the polyhedrin promoter followed by the polyadenylation signal of the polyhedrin gene. The polyhedrin sequences in this vector are flanked at both sides by viral sequences for the cell-mediated homologous recombination of cotransfected wild-type viral DNA. Many other baculovirus vectors could be used in place of pRG1 such as pAc373, pVL941 and pAcIMI (Luckow, V. A. & Summers, M. D., *Virology* 170:31–39).

The plasmid was digested with the restriction enzymes BamHI and Asp781 and then dephosphorylated using calf intestinal phosphatase by procedures known in the art. The DNA was then isolated from a 1% agarose gel using a commercially available kit ("Geneclean" BIO 101 Inc., La Jolla, Calif.). This vector DNA was designated V2.

Fragment F2 and the dephosphorylated plasmid V2 were ligated with T4 DNA ligase. *E. coli* HB1O1 cells were then transformed and bacteria identified that contained the plasmid (pBac-LAI-1) with the LAI-1 gene using the enzymes BamHI and Asp78 1. The sequence of the cloned fragment was confirmed by DNA sequencing.

5 µg of the plasmid pBac-LAI-1 was cotransfected with 1.0 µg of a commercially available linearized baculovirus ("BaculoGold™ baculovirus DNA", Pharmingen, San Diego, Calif.) using the lipofection method (Felgner et al., *Proc. Natl. Acad Sci. USA* 84:7413–7417 (1987)).

1 µg of BaculoGold™ virus DNA and 5 µg of the plasmid pBac-LAI-1 were mixed in a sterile well of a microliter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-LAI-1 at a multiplicity of infection (MOI) of 2. Six hours later the medium was removed and replaced with SF900 II medium minus methionine and cysteine (Life Technologies Inc., Gaithersburg, Md.). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

Several batches were obtained. In batch B1, about 50% of the protein was determined to have an N-terminus of Val (23)-Leu (24)-Glu(25) . . . ; about 10% to have Val(26)-Tyr (27)-Tyr(28) . . . ; about 20% to have Thr(29)-Ser(30)-Leu(3 1) . . . ; and about 20% to have Ser(30)-Leu(3 1)-Arg(32) . . . .

In batch B2, about 95% of the protein was determined to have an N-terminus of Val(23)-Leu (24)-Glu(25) . . . .

In batch B3 about 35% of the protein was determined to have an N-terminus of Val(23)-Leu (24)-Glu(25) . . . ; about 20% to have Val(26)-Tyr(27)-Tyr(28) . . . ; and about 35% to have Ser(30)-Leu(31)-Arg(32) . . . .

In batch B4, about 96% of the protein was determined to have an N-terminus of Val(23)-Leu (24)-Glu(25) . . . .

In batch B5, about 5% of the protein was determined to have an N-terminus of Val(23)-Leu (24)-Glu(25) . . . ; about 10% to have an N-terminus of Val(26)-Tyr( 27)-Tyr(28) . . . ; about 30% to have an N-terminus of Thr(29)-Ser(30)-Leu(3 1) . . . ; and about 40% to have an N-terminus of Ser(30)-Leu(3 1)-Arg(32) . . . .

In batch B6, about 96% of the protein was determined to have an N-terminus of Val(23)-Leu (24)-Glu(25) . . . .

EXAMPLE 7
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks. pMV-7 (Kirschmeier et al., DNA 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA3 17 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 8
Chemotaxis:

Peripheral blood mononuclear cells were purified from donor leukopacks (Red Cross) by centrifugation on lymphocyte separation medium (LSM; density 1.077 g/ml; Organon Teknika Corp.) and harvesting the interface band. Granulocytes were recovered from the pellet following a dextran sedimentation step prior to ficol separation. Monocytes were purified by elutriation and T-lymphocytes purified from the PBMCs using T-cell enrichment columns (R&D Systems). For activation of the T-lymphocytes, cells were stimulated by crosslinking through the CD3 receptor in the presence of IL-2 (10 U/ml) for 16 hours prior to the chemotaxis assay.

Cells used for the assay were washed 3X with HBSS/0.1% BSA and resuspended at $2 \times 10^6$/ml for labeling. Calcein-AM (Molecular Probes) was added to a final concentration of 1 tM and the cells incubated at 37° C. for 30 minutes. Following this incubation the cells were washed 3X with HBSS/0.1% BSA. Labeled cells were resuspended as $4-8 \times 10^6$/ml and 25μl ($1-2 \times 10^5$ cells) added to the top of a polycarbonate filter (3–5 μm pore size; PVP free; NeuroProbe, Inc.) which separates the cell suspension from the chemotactic agent in the plate below. Cells are allowed to migrate for 45–90 minutes and then the number of migrrated cells (both attached to the filter as well as in the bottom plate) are quantitated using a Cytofluor II fluorescence plate reader (PerSeptive Biosystems).

EXAMPLE 9
LAI-1 inhibits PBMC adhesion

Chemotaxis, Adhesion and Cell surface staining. Human peripheral blood mononuclear cells (PBMCs) and polymorphonucleated neutrophil cells (PMNs) were purified from single donor leukopacks (Red Cross) according to established methods. Monocytes were purified by elutriation. Primary human umbilical vein endothelial cells were isolated from healthy donors also following established methods. Target cells used for the chemotaxis and adhesion assays were washed three times in HBSS with 0.1% BSA (HBSS/BSA) and resuspended at $2 \times 10^6$/ml for labeling. Calcein-AM (Molecular Probes) was added to a final concentration of 1 μM and the cells incubated at 37° C. for 30 minutes. Following this incubation the cells were washed three times in HBSS/BSA.

For the chemotaxis assays, labeled cells were resuspended as $4-8 \times 10^6$/ml and 25 μl ($1-2 \times 10^5$ cells) added to the top of a polycarbonate filter (3–5 μm pore size; PVP free; NeuroProbe, Inc.) which separates the cell suspension from the chemotactic agent in the plate below. Cells were allowed to migrate for 45–90 minutes and then the number of migrated cells (both attached to the filter as well as in the bottom plate) were quantitated using a Cytofluor II fluorescence plate reader (PerSeptive Biosystems). For the adhesion assays, primary HUVEC cells were plated into 48 well dishes, allowed to reach near confluency and then used immediately or treated with various test factors prior to the adhesion assay. Labeled target cells were plated onto the 48 well dishes containing the monolayer of primary HUVEC cells in the presence or absence of test factors. The cells were allowed to attach to the HUVEC cells in RPMI/0.1% BSA for 45–90 minutes, and the plate was then washed and the bound cells quantitated in a Cytofluor II. Direct and indirect cell surface staining was performed using established methods and the cells analyzed on a Becton Dickinson FACScan.

Figure 4:
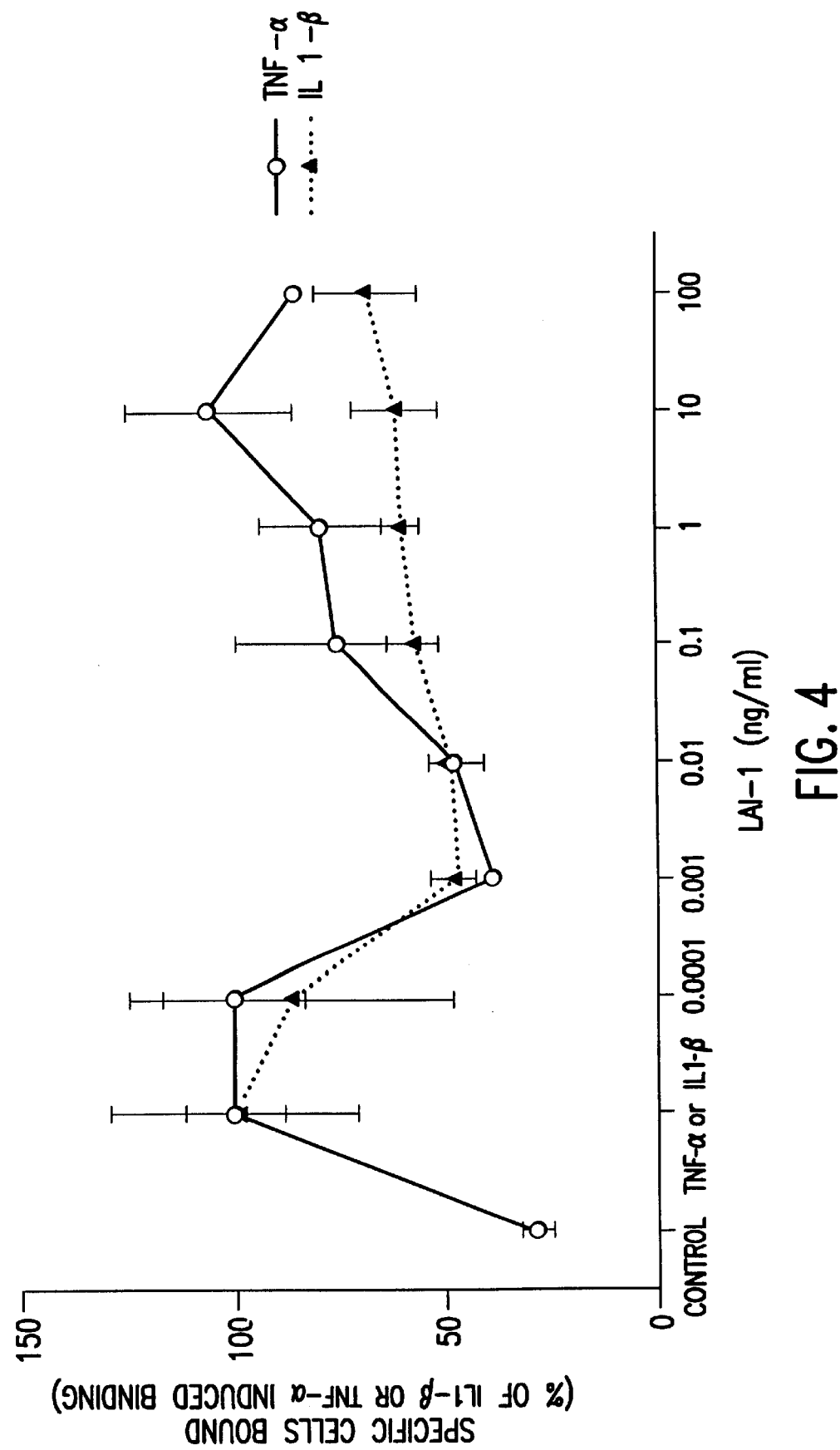
FIG. 4 shows data representing that LAI-1 inhibits PBMC adhesion to ILL-β or TNF-α induced HUVEC monolayers. Human peripheral blood mononuclear cells (PBMCs) were used in adhesion assays with primary HUVEC monolayers as described in the materials and methods section. As shown, the addition of LAI-1 during the adhesion assay caused a bi-phasic, dose dependent inhibition of PBMC adhesion to endothelial cell monolayers which were activated with IL1-β (closed triangles) or with TNF-α (open circles). The maximal effect of LAI-1 was observed at 1–10 pg/ml. Data shown represents the specific cells bound as a percentage of the maximal binding seen with IL1-β or TNF-α +/− the standard deviation of triplicate samples.

FIG. 4 shows data representing that LAI-1 inhibits PBMC adhesion to ILL-β or TNF-α induced HUVEC monolayers. Human peripheral blood mononuclear cells (PBMCs) were used in adhesion assays with primary HUVEC monolayers as described above. As shown, the addition of LAI-1 during the adhesion assay caused a bi-phasic, dose dependent inhibition of PBMC adhesion to endothelial cell monolayers which were activated with IL1-β (closed triangles) or with TNF-α. (open circles). The maximal effect of LAI-1 was observed at 1–10 μg/ml. Data shown represents the specific cells bound as a percentage of the maximal binding seen with IL1-β or TNF-α +/– the standard deviation of triplicate samples.

Figure 5A:
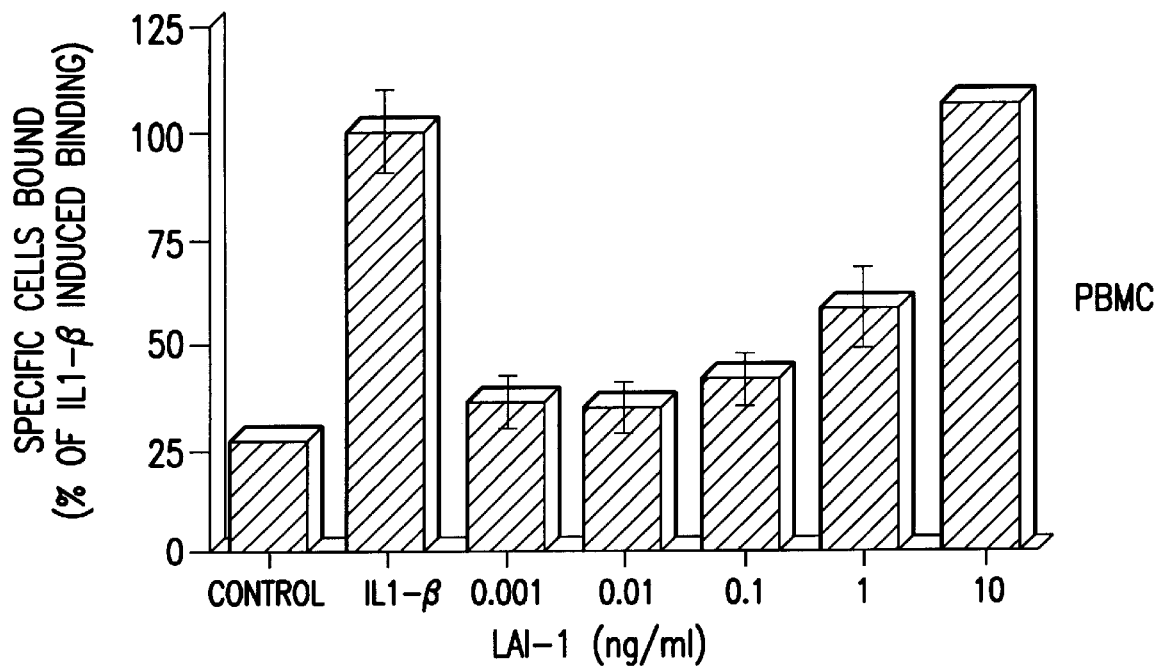
FIG. 5A–B shows data representing that LAI-1 inhibits PBMC (FIG. 5A), but not PMN (FIG. 5B) adhesion to IL1-β activated HUVEC Cells. PBMCs (FIG. 5A) and polymorphonucleated neutrophil cells (PMNS) (FIG. 5B) were used for adhesion assays with IL1-β activated C monolayers. As shown, addition of LAI-1 to the adhesion assay resulted in the inhibition of PBMC adhesion to the HUVEC monolayer but had no effect on the adhesion of neutrophils in the same assay. Data shown represents the specific cells bound as a percentage of the maximal binding seen with IL1-β +/− the standard deviation of triplicate samples.
Figure 5B:
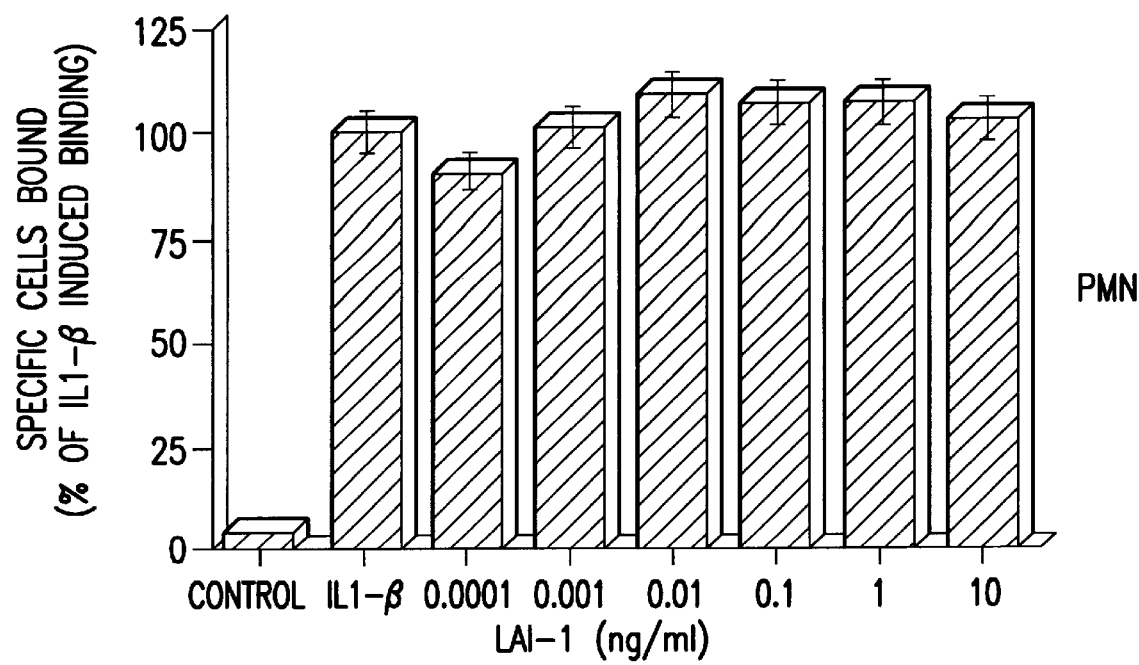

FIG. 5A–B shows data representing that LAI-1 inhibits PBMC (FIG. 5A), but not PMN (FIG. 5B) adhesion to IL1-β activated HUVEC Cells. PBMCs (FIG. 5A) and polymorphonucleated neutrophil cells (PMNS) (FIG. 5B) were used for adhesion assays with IL1-β activated C monolayers. As shown, addition of LAI-1 to the adhesion assay resulted in the inhibition of PBMC adhesion to the HUVEC monolayer but had no effect on the adhesion of neutrophils in the same assay. Data shown represents the specific cells bound as a percentage of the maximal binding seen with IL1-β +/– the standard deviation of triplicate samples.

Figure 6A:
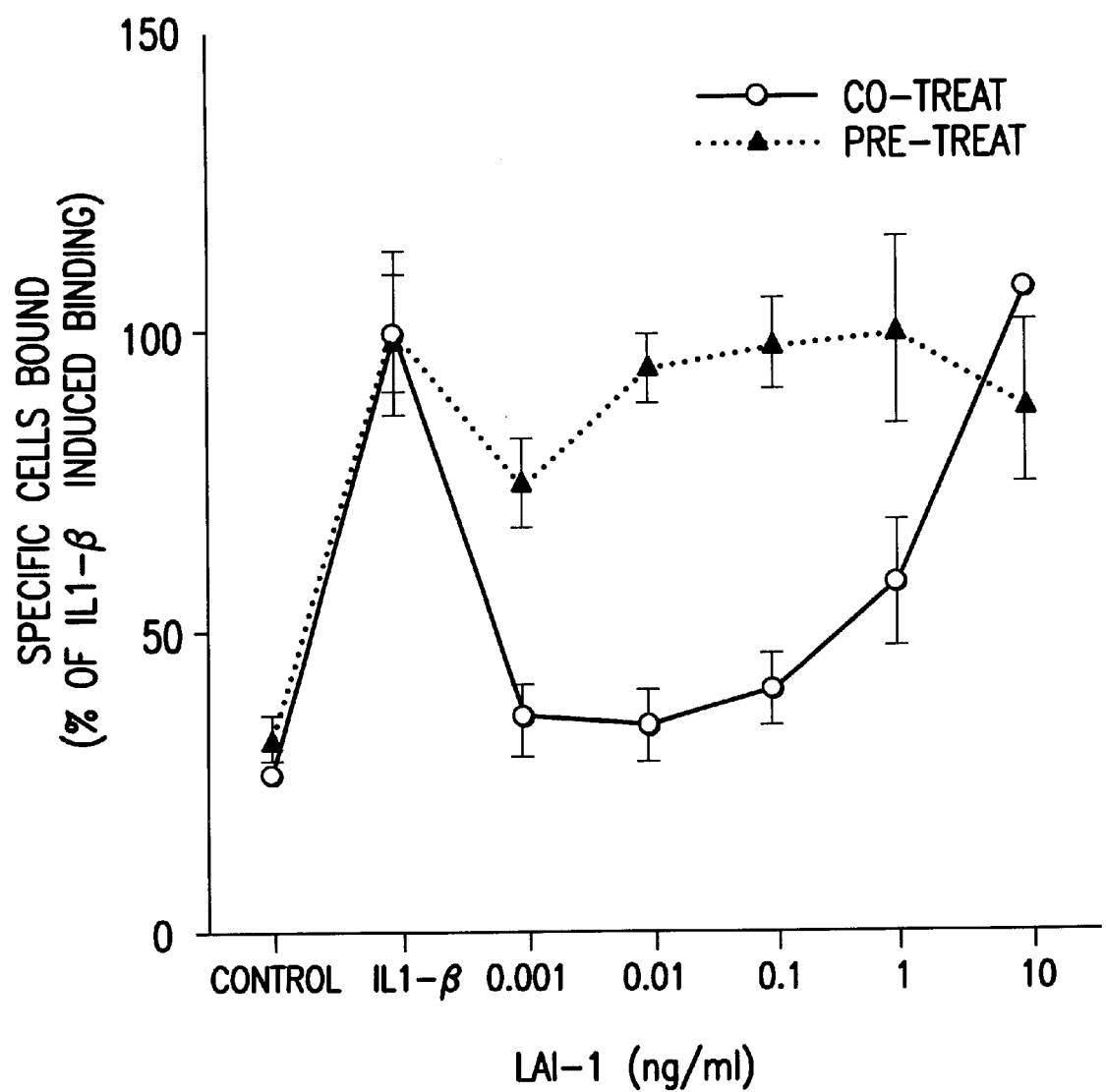
FIG. 6A–B shows data representing that the pre-treatment of PBMCs with LAI-1 inhibits subsequent adhesion to ILL-P activated HUVEC Cells.
Figure 6B:
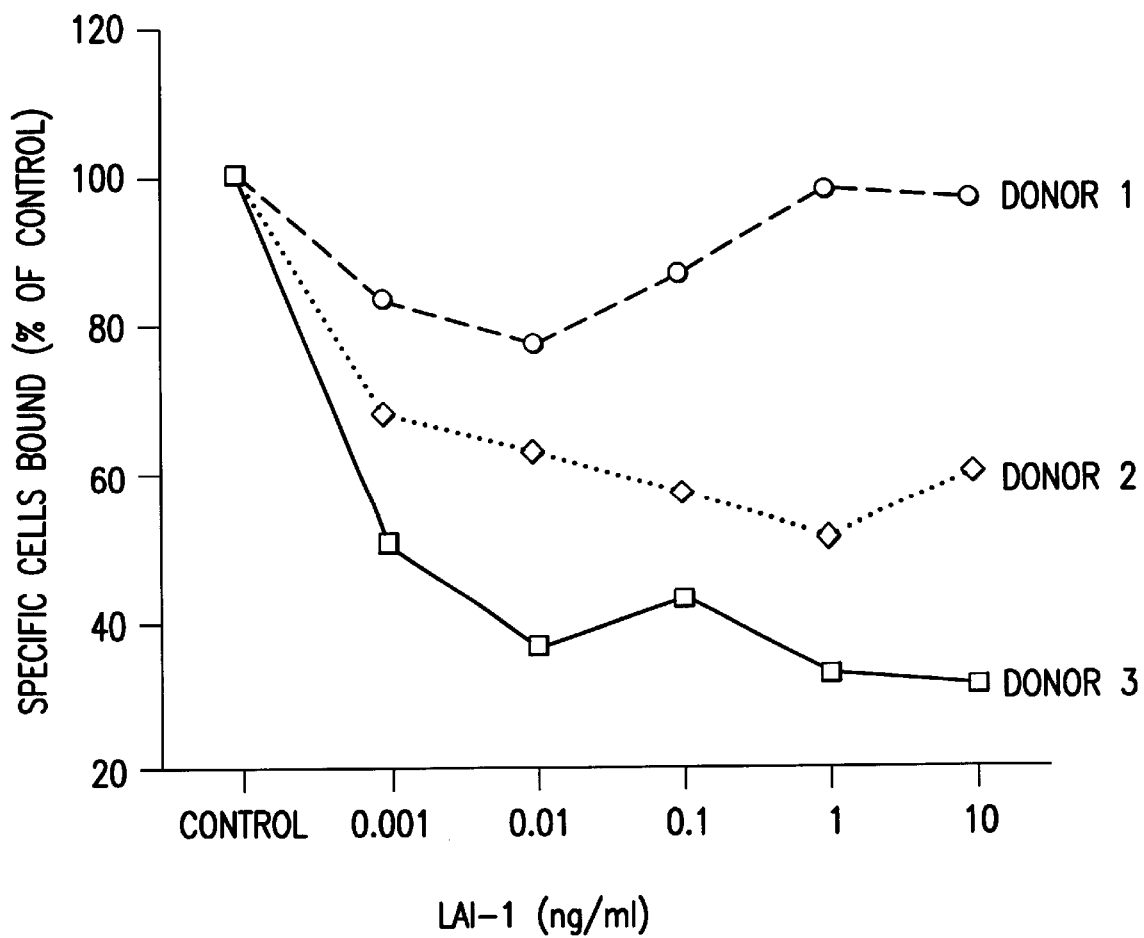

FIG. 6A–B shows data representing that the pre-treatment of PBMCs with LAI-1 inhibits subsequent adhesion to ILL-P activated HUVEC Cells. In FIG. 6A, the ILl-β activated C monolayer was either pre-treated with LAI-1 (closed triangles) which was then washed away or had LAI-1 added during the adhesion assay (open circles) as described in FIG. 4. As shown, pre-treatment of the HUVEC monolayer with LAI-1 had no significant effect on the subsequent adhesion of PBMCS. Within this same assay, LAI-1 was still able to inhibit PBMC adhesion when present during the adhesion assay. FIG. 6B shows three separate donor PBMCs were pre-treated with LAI-1 at the concentrations indicated and the pre-treated cells monitored for their capacity to bind to an IL1-β activated HUVEC monolayer in the absence of any added LAI-1 during the assay. As shown, pre-treatment of the PBMCs with LAI-1 resulted in a reduction in binding ranging from 20 to 60% of that seen with the untreated PBMCS.

Figure 7A:
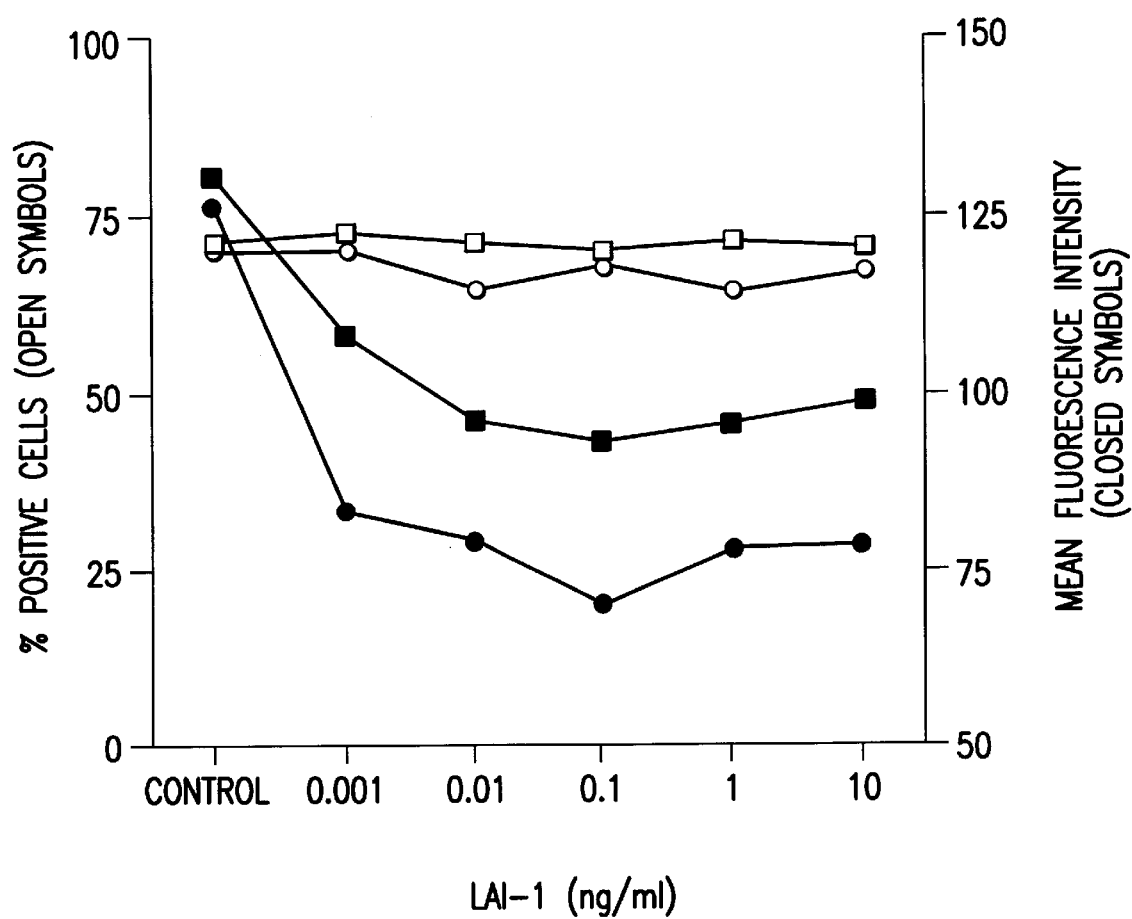
FIG. 7A–B shows data representing a decrease in the mean fluorescence intensity of CD29 on PBMCs treated with LAI-1. PBMCs from two donors were treated for 4 hours with LAI-1 at the concentrations indicated and then stained for surface expression of CD11b, CD11c, CD29, CD54, CD49d, CD49e, and CD106. The only significant differences noted were with CD29.
Figure 7B:
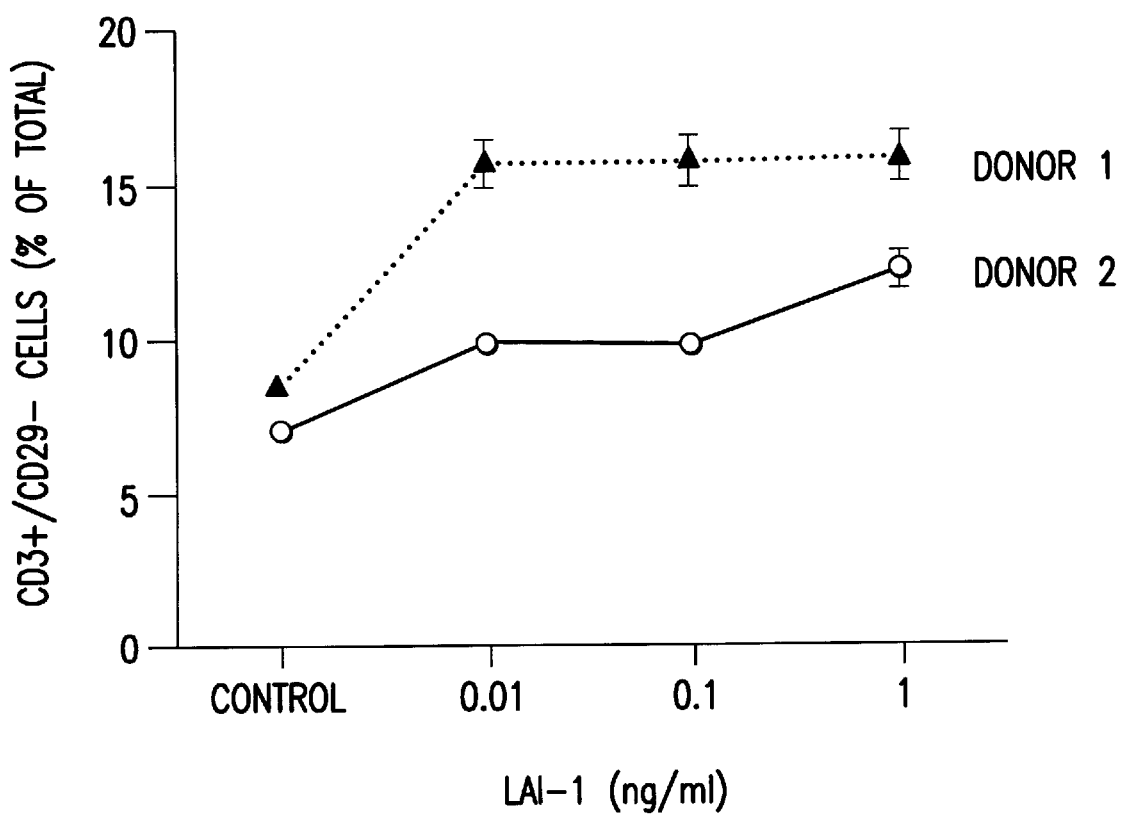
Figure 8A:
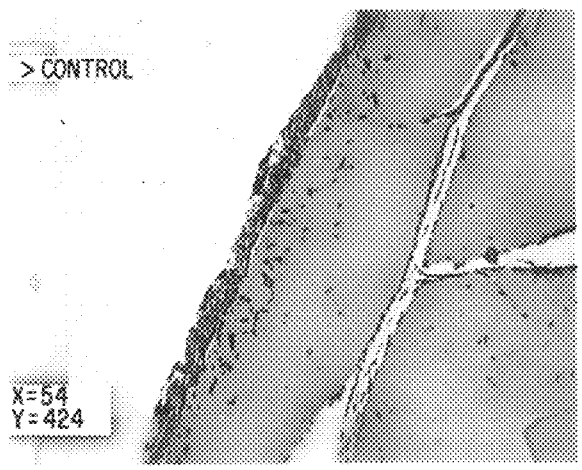
FIG. 8A–D are photographic representations showing that Anti-vWF immunostaining of histological sections of Matrigel plugs treated with bFGF, LAI-1 revealed a near total inhibition of the vWF-positive endothelial cells in large vessels and blood sinuses numerous in the bFGF-treated positive control (FIG. 8A). The Matrigel was mixed with inactive protein control (FIG. 8A), bFGF (150 ng/ml) alone (FIG. 8B), bFGF (150 ng/ml)+LAI-1(500 ng/ml) (FIG. 8C), bFGF (150 ng/ml)+IP-10 (500 ng/ml) (FIG. 8D).
Figure 8B:
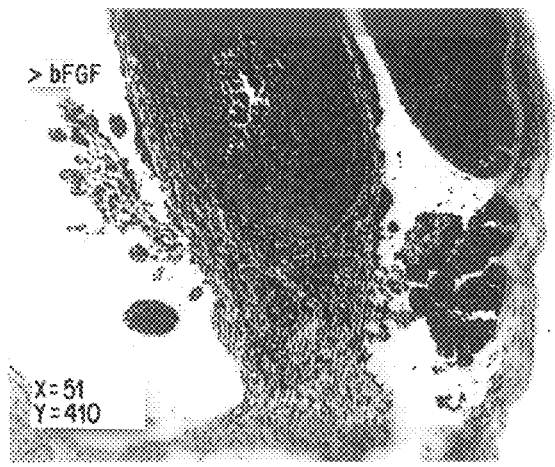
Figure 8C:
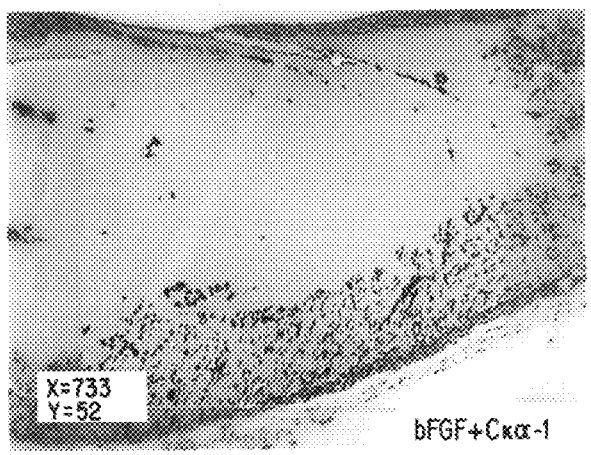
Figure 8D:
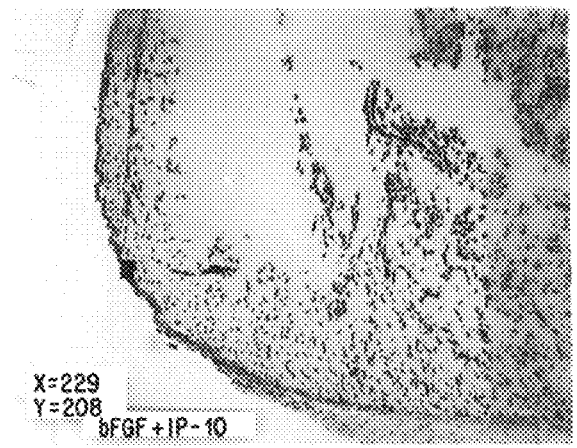

FIG. 7A–B shows data representing a decrease in the mean fluorescence intensity of CD29 on PBMCs treated with LAI-1. PBMCs from two donors were treated for 4 hours with LAI-1 at the concentrations indicated and then stained for surface expression of CD11b, CD11c, CD29, CD54, CD49d, CD49e, and CD106. The only significant differences noted were with CD29. As shown in FIG. 7A, there was no effect on the percentage of cells which stained positive for CD29 (open symbols). However, the mean fluorescence intensity of the CD29 signal was reduced in both donors when the PBMCs were exposed to LAI-1 (closed symbols). This decrease in CD29 mean fluorescence was evident within a CD3 gated population of PBMCs but not in a CD20, CD56, or CD 14 gated population. In addition, as shown in FIG. 7B, LAI-1 treatment caused an increase in the percentage of CD3+/CD29− cells.

EXAMPLE 10

LAI-1, a novel C—X—C Clemokine Which Inhibits Leukocyte Adhesion to Activated Endothelium A novel C—X—C (alpha) chemokine, LAI-1, was identified, cloned and functionally characterized. LAI-1 mRNA is constitutively expressed in the liver and spleen but not in a variety of other tissues assayed. LAI-1 encodes a protein of 109 amino acids of which the first 22 represent the leader sequence. Although LAI-1 is a member of the alpha-chemokine family, it shows very limited homology to the other known members. Similar to IP-10, it also lacks the ELR motif (having instead the SLR motif) present in other alpha family-chemokines and shows no significant chemotactic activity on neutrophils. In adhesion assays using IL-1β or TNF-β activated HUVEC monolayers, LAI-1 specifically decreased the adhesion of peripheral blood leukocytes and has therefore been named Leukocyte Adhesion Inhibitor-1, or LAI-1. The ability of LAI-1 to block leukocyte adhesion to HUVEC monolayers appears to be directed towards the leukocytes since LAI-pre-treatment of HUVEC cells had no effect on subsequent adhesion capacity. Furthermore, pre-treatment of leukocytes with LAI-1 was enough to inhibit their adhesion to an activated endothelial layer. Based on co-culture experiments with leukocytes, it appears that LAI-1 can actually decrease P1 integrin levels on leukocytes and this can explain their decreased adhesive properties.

EXAMPLE 11

In vivo angiogenesis assay of LAI-1 (Ckα-1)

This bioassay measures the ability of an existing capillary network to form new vessels in an implanted capsule of murine extracellular matrix-material (Matrigel). HGS proteins are mixed with the liquid Matrigel at 4° C. and the mixture is then injected subcutaneously in mice where it solidifies. After 7 days, the solid "plug" of Matrigel is removed and examined for the presence of new blood vessels. Assay:

Matrigel was purchased from Becton Dickinson Labware/ Collaborative Biomedical Products. When thawed at 4° C. this material is a liquid. The Matrigel was mixed with bFGF (150 ng/ml) alone, bFGF (150 ng/ml)+LAI-1(500 ng/ml) or bFGF (150 ng/ml)+IP-10 (500 ng/ml) at 4° C. and drawn into cold 3 ml syringes. Female C57B1/6 mice approximately 8 weeks old were injected with the mixture of Matrigel and experimental protein at 2 sites at the midventral aspect of the abdomen (0.5 ml/site). After 7 days, the mice were sacrificed by cervical dislocation, the Matrigel plugs were removed and cleaned (i.e., all clinging membranes and fibrous tissue is removed). Replicate whole plugs were fixed in neutral buffered 10% formaldehyde, embedded in paraffin and used to produce sections for histological examination after staining with Masson's Trichrome. Cross sections from 3 different regions of each plug were processed. Selected sections were stained for the presence of vWF (an endothelial cell-specific marker). The positive control for this assay was bovine basic FGF (150 ng/ml). Matrigel alone was used to determine basal levels of angiogenesis.

Results:

Basic FGF induced marked vascularization of the Matrigel plug as analyzed by visual inspection of the dissected plugs and examination of histological sections of the plugs. LAI-1 inhibited the bFGF-induced accumulation of blood in the plugs by greater than 90% as estimated by visual inspection of the intact plugs and histological sections. Anti-vWF immunostaining of histological sections of Matrigel plugs treated with BFGF and LAI-1 revealed a near total inhibition of the vWlF-positive endothelial cells in large vessels and blood sinuses numerous in the BFGF-treated positive control (FIG. 8A–D).

| angiostimulatory protein | angiogenic activity |
| --- | --- |
| bFGF (FIG. 8B) | +++++ |
| bFGF + LAI-1 (FIG. 8C) | + |
| bFGF + IP-10 (FIG. 8D) | + |
| no protein control (FIG. 8A) | − |

These results show that LAI-1 polypeptides and agonists of the present invention have anti-angiogenic activity in vivo and are therefore useful in treating pathologies that are associated with, or involve increased vascularization. Such pathologies or disorders include, but are not limited to, cancers that involve increased vascularization; inflammation involving vascularized tissue; or any disorders that involve, or rely on, vascularization, as is well known in the art.

Similarly, these results indicate that LAI-1 polypeptide antagonists or LAI-1 variants having antagonistic activity have angiogenic activity. Such activities include, but are not limited to wound healing, revascularization, and/or any disorders that can be treated by increasing vascularization (e.g., diabetes), as are well known in the art. Such antagonists include an LAI-1 variant containing at least a substution of Glu30 for Ser30.

EXAMPLE 12
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g. Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al, *DNA* 7:219–25 (1988) flanked by the long terminal repeats of the Moloney murine sarcoma virus, is digested with EcoRi and HindIII and subsequently treated with calf intestinal phosphatase. The linear vector is fractionated on agarose gel and purified, using glass beads.

The cDNA encoding a Ck beta-11 or LAI-1 polypeptide or variant of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbeccol's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 13
LAI-1 as a Chemoattractantfor T-lymphocytes in vivo.

Female Balb/c mice, 4–6 weeks old are put into 4 groups of ten animals per group. The groups are either untreated, injected intraperitoneally with vehicle control or injected with LAI-1 at 1 mg/kg or 3 mg/kg for 6 consecutive days. On day seven, the mice are sacrificed and peritoneal cavity lavage performed to collect the resident cells. Total cell numbers are calculated and the cells subjected to cell surface staining using the following panel of monoclonal antibodies: CD3, CD4, CD8, Mac1, GR1, B220, MHC class II, CD14, CD45, and CD5 (Pharmingen, San Diego, CA).

The total cell numbers within the peritoneal cavity are expected to significantly increased over untreated or vehicle treated controls. This is expected to be due to an influx of T-lymphocytes as determined by cell surface staining for CD4, CD5, and CD8. There is expected a dramatic increase in CD4 positive cells as well as CD5 and CD8 cells resulting in a net increase in the relative number of T-lymphocytes. In addition, there is expected a significant increase in Mac1 positive, MHC class II negative, subpopulation of cells within the peritoneal cavity with a corresponding decrease in the percentage of MHC class II positive, Mac1 positive subpopulation of cells. This is also reflected in the total number of MHC class II negative, MacI positive cells within the peritoneal cavity .

LAI-1 is thus expected to shown to be a chemoattractant for T-lymphocytes in vivo. This could be for CD4, CD8 or both subpopulations of T-cells. Based on this, LAI-1 can be beneficial for disease states which would benefit from the attraction and/or activation of this population of immune cells. This would include bacterial or viral infection, cancer, and the like. Also, if LAI-1 has a specific effect on the Th1 or Th2 subclass of CD4 lymphocytes, it could bias the normal production of cytokines from these cells and dramatically influence other immune cells such as monocytes, macrophages, eosinophils, and other immune cells.

EXAMPLE 14
Purification of LAI-1
Purification from CHO Expression System

Following expression of LAI-1 in Chinese hamster ovary cells, the protein is purified using the following procedure. All of the purification procedures are performed at 5–10° C., unless otherwise specified. The transfected CHO cells are grown in HGS-CHO-3 medium using the microcarrier culture system (cytodex I, Pharmacia) for 4 days. The conditioned media are harvested using low speed centrifugation to remove cells and cell debris. After pH is adjusted to 7.0 with acetic acid, the conditioned media is loaded onto a strong cation exchange column (Poros HS-50, Perseptive Biosystems Inc.) pre-equilibrated with phosphate buffered saline (PBS), pH 7.0. The column is then washed with same buffer until the absorbance at 280 nm is less than 0.01 O.D. (10 CV). The desired protein is eluted by washing the column with 1 M NaCl in phosphate buffered saline, pH 7.0. Fractions are then analyzed by SDS-PAGE through 4–20% gradient gels to confirm the presence of the desired polypeptide.

Those fractions containing LAI-1 are then pooled and loaded onto a gel filtration column of Superdex-75 resin (Pharmacia) equilibrated in "sizing buffer" comprising 50 mM sodium acetate and 150 mM NaCl, pH 6.0. The sample loaded is less than 10% (V/V) of the column volume. After allowing the sample to run into the column, the protein is eluted from the gel filtration matrix using the same buffer. Fractions are collected and the absorbance at 280 nm of the effluent is continuously monitored. Fractions identified by A280 as containing eluted material are then analyzed by SDS-PAGE. Fractions containing LAI-1 is eluted in a peak centered at 0.62 column volumes and pooled.

The pooled fractions from gel filtration chromatography is applied onto a set of strong anion (Poros HQ-50, Perseptive Biosystems) and weak anion (Poros CM-20) exchange columns in a tandem mode. Both columns are pre-equilibrated and washed with 50 mM sodium acetate buffer, pH 6.0 after sample loading. The cation exchange column (CM-20) is then washed with 0.3M NaCl followed by a 0.3M to 0.8M NaCl gradient elution in the same buffer system. The eluted fractions are analyzed through SDS-PAGE and fractions containing protein of interest are combined.

Following the purification steps described above, the resultant LAI-1 is of greater than 95% purity as determined from Commassie blue staining of a SDS-PAGE gel. The purified protein is also tested for endotoxin/LPS contamination. The LPS content is less than 0.1 ng/mg of purified protein according to LAL assays.

An alternative purification procedure is also used to purify LAI-1. The procedure involves the following steps, and unless otherwise specified, all procedures are conducted at 5–10° C.

Upon completion of the production phase of a CHO culture, the conditioned media are obtained after cells/cell debris removal using low speed centrifugation. Following pH of the media being adjusted to pH 7.0 by adding acetic acid, the media are loaded onto a strong cation exchange column (Poros HS-50, Perspective Biosystems, Inc.) pre-equilibrated with phosphate buffered saline (PBS), pH 7.0. The column is then washed with same buffer until the absorbance at 280 nm is less than 0.01 O.D. (10 CV). The desired protein is eluted by ishing the column with 1 M NaCl in phosphate buffered saline, pH 7.0. Fractions are then analyzed by SDS-PAGE through 4–20% gradient gels to confirm the presence of the LAI-1.

Those fractions containing LAI-1 are then pooled, followed by the addition of 4 volumes of 10 mM sodium acetate, pH 6.5. The diluted sample is then loaded onto a previously prepared set of tandem columns of strong anion (Poros HQ-50, Perseptive Biosystems) and weak anion (Poros CM-20, Perceptive Biosystems) exchange resin. The columns are equilibrated with 50 mM sodium acetate pH 6.5. The CM-20 column is washed with 5 column volumes of 0.2 M NaCl, 50 mM sodium acetate, pH 6.5 and eluted using a 10 column volume linear gradient ranging from 0.2M NaCl, 50 mM sodium acetate, pH 6.5 to 1.0 M NaCl 50 mM sodium acetate, pH 6.5. Fractions are collected under constant A280 monitoring of the effluent. Those fractions containing the protein of interest (determined by 4–20% SDS-PAGE) are then pooled.

The combined fractions containing LAI-1 are then loaded (V/V, 5% of the column volume) onto a sizing exclusion column (Superdex-75, Pharmacia) equilibrated with 100 mM NaCl, 50 mM sodium acetate, pH 6.5. After allowing the sample to run into the column, the protein is eluted from the gel filtration matrix using 100 mM NaCl, 50 mM sodium acetate, pH 6.5. Fractions are collected and the absorbance at 280 nm of the effluent is continuously monitored. Fractions identified to $A_{280}$ as containing the eluted material are then analyzed by SDS-PAGE. Fractions containing LAI-1 is then pooled.

Following the three step purification procedure described above, the resultant LAI-1 is of greater than 95% purity as determined from Commassie blue staining of a SDS-PAGE gel. The purified protein is also tested for endotoxin/LPS contamination. The LPS content is less than 0.1 ng/mg of purified protein according to LAL assays.

Purification of LAI-1 from *E. coli*

The purification involves the following steps, and unless otherwise specified, all procedures are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous solution using a high shear mixer.

The cells are then lysed by passing the solution through microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000 g f or 15 min. The resulted pellet is washed again using 0.5M NaCl, 100 mM Tris, 50 mM EDTA, pH 7.4.

The washed inclusion body is solubilized with 1.5 M Guanidine hydrochloride (GuHCI) for 2–4 hours. After 7000 g centrifugation for 15 min., pellet is discarded and the LAI-1-containing supernatant is placed at 4° C. overnight for further GuHCl extraction.

Following high speed centrifugation (30000 g) to remove the insoluble particles, the GuHCl solubilized proteins are refolded by quickly mixing the GuHCl extraction with 20 volumes of buffer containing 50 mM sodium, pH 4.5, 150 mM NaCl, 2 mM EDTA by vigorous stirring. The refolded diluted protein solution is set kept at 4° C. without mixing for 12 hours prior to further purification steps.

To clarify the refolded LAI-1 solution, a previously prepared tangential filtration unit equipped with 0.16 urn membrane filter with appropriate surface area (Filtron), equilibrated with 40 mM sodium acetate, pH 6.0 is employed. The filtered sample is loaded onto a cation exchange of poros HS-50 resin (Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Those fractions contained desired protein is then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resin. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2M NaCl, 50 mM sodium acetate, pH 6.0 to 1.0M NaCl, 50 mM sodium acetate, pH 6.5. Fractions are collected under constant A280 monitoring of the effluent. Those fractions containing the protein of interest (determined by 16% SDS-PAGE) are then pooled.

The resultant LAI-1 is of greater than 95% purity after the above refolding and purification steps. No major contaminant bands are observed from the Commassie blue stained 16% SDS-PAGE gel when 5 μg of purified protein is loaded.

The purified protein is also tested for endotoxin/LPS contamination. The LPS content is expected to be less than 0.1 ng/ml according to LAL assays.

The above methods can be similarly applied to purification of similarly expressed Ck beta-11 polpeptides with suitable results.

It will be clear that the invention can be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are entirely hereby incorporated by reference.

What at is claimed is:

1. An isolated polypeptide consisting of amino acid residues selected from the group consisting of:

(a) Gly (22)-Pro (109) of SEQ ID NO:4;
(b) Leu (24)-Pro (109) of SEQ ID NO:4;
(c) Glu (25)-Pro (109) of SEQ ID NO:4;
(d) Val (26)-Pro (109) of SEQ ID NO:4;
(e) Tyr (27)-Pro (109) of SEQ ID NO:4;
(f) Tyr (28)-Pro (109) of SEQ ID NO:4;
(g) Thr (29)-Pro (109) of SEQ ID NO:4;
(h) Ser (30)-Pro (109) of SEQ ID NO:4;
(i) Val (23)---Pro (102) of SEQ ID NO:4;
(j) Val (23)---Val (101) of SEQ ID NO:4;
(k) Val (23)---Pro (100) of SEQ ID NO:4;
(l) Val (23)---Leu (99) of SEQ ID NO:4;
(m) Val (23)---Thr (98) of SEQ ID NO:4;
(n) Val (23)---Ser (97) of SEQ ID NO:4;
(o) Val (23)---Ser (96) of SEQ ID NO:4;
(p) Val (23)---Ser (95) of SEQ ID NO:4;
(q) Val (23)---Arg (94) of SEQ ID NO:4;
(r) Val (23)---Lys (93) of SEQ ID NO:4;
(s) Val (23)---Arg (92) of SEQ ID NO:4;
(t) Val (23)---Leu (91) of SEQ ID NO:4;
(u) Val (23)---Val (90) of SEQ ID NO:4;
(v) Val (23)---Glu (89) of SEQ ID NO:4;
(w) Val (23)---Met (88) of SEQ ID NO:4;
(x) Val (23)---Met (87) of SEQ ID NO:4;
(y) Val (23)---Arg (86) of SEQ ID NO:4;
(z) Val (23)---Gin (85) of SEQ ID NO:4,
(aa) Val (23)---Ile (84) of SEQ ID NO:4;
(bb) Val (23)---Trp (83) of SEQ ID NO:4;
(cc) Val (23)---Glu (82) of SEQ ID NO:4;
(dd) Val (23)---Ala (81) of SEQ ID NO:4;
(ee) Val (23)---Gin (80) of SEQ ID NO:4;
(ff) Val (23)---Pro (79) of SEQ ID NO:4;
(gg) Val (23)---Asp (78) of SEQ ID NO:4;
(hh) Val (23)---Val (77) of SEQ ID NO:4;
(ii) Val (23)---Cys (76) of SEQ ID NO:4;
(jj) Leu (24)-Ile (108) of SEQ ID NO:4;
(kk) Glu (25)-Lys (107) of SEQ ID NO:4;
(ll) Val (26)---Arg (106) of SEQ ID NO:4;
(mm) Tyr (27)---Lys (105) of SEQ ID NO:4;
(nn) Tyr (28)---Phe (104) of SEQ ID NO:4;
(oo) Thr (29)---Val (103) of SEQ ID NO:4;
(pp) Scr (30)---Lys (107) of SEQ ID NO:4;
(qq) Ser (30)---Lys (105) of SEQ ID NO:4;
(rr) Ser (30)---Lys (93) of SEQ ID NO:4; and
(ss) Ser (30)---Cys (76) of SEQ ID NO:4.

2. The isolated polypeptide of claim 1, which is produced by a recombinant cell.

3. The isolated polypeptide of claim 2, wherein said recombinant cell is *E. coli.*

4. The isolated polypeptide of claim 2, wherein said recombinant cell is a COS cell.

5. The isolated polypeptide of claim 2, which is produced recombinantly using a baculovirus system.

6. The isolated polypeptide of claim 1, fused to a heterologous polypeptide.

7. A composition comprising the isolated polypeptide of claim 1 and a pharmaceutically acceptable carrier.

8. An isolated polypeptide consisting of a methionine residue at the N-terminus plus amino acid residues selected from the group consisting of:

(a) Gly (22)-Pro (109) of SEQ ID NO:4;
(b) Leu (24)-Pro (109) of SEQ ID NO:4;
(c) Glu (25)-Pro (109) of SEQ ID NO:4;
(d) Val (26)-Pro (109) of SEQ ID NO:4;
(e) Tyr (27)-Pro (109) of SEQ II) NO:4;
(f) Tyr (28)-Pro (109) of SEQ ID NO:4;
(g) Thr (29)-Pro (109) of SEQ ID NO:4;
(h) Ser (30)-Pro (109) of SEQ ID NO:4;
(i) Val (23)---Pro (102) of SEQ ID NO:4;
(j) Val (23)---Val (100) of SEQ IDNO:4;
(k) Val (23)---Pro (100) of SEQ ID NO:4;
(l) Val (23)---Leu (99) of SEQ ID NO:4;
(m) Val (23)---Thr (98) of SEQ ID NO:4;
(n) Val (23)---Ser (97) of SEQ ID NO:4;
(o) Val (23)---Ser (96) of SEQ ID NO:4;
(p) Val (23)---Ser (95) of SEQ ID NO:4;
(q) Val (23)---Arg (94) of SEQ ID NO:4;
(r) Val (23)---Lys (93) of SEQ ID NO:4;
(s) Val (23)---Arg (92) of SEQ ID NO:4;
(t) Val (23)---Leu (91) of SEQ ID NO:4;
(u) Val (23)---Val (90) of SElQ ID NO:4;
(v) Val (23)---Glu (89) of SEQ ID NO:4;
(w) Val (23)---Met (88) of SEQ ID NO:4;
(x) Val (23)---Met (87) of SEQ ID NO:4;
(y) Val (23)---Arg (86) of SEQ ID NO:4;
(z) Val (23)---Gln (85) of SEQ ID NO:4;
(aa) Val (23)---Ile (84) of SEQ ID NO:4;
(bb) Val (23)---Trp (83) of SEQ ID NO:4;
(cc) Val (23)---Glu (82) of SEQ ID NO:4;
(dd) Val (23)---Ala (81) of SEQ ID NO:4;
(ee) Val (23)---Gln (80) of SEQ ID NO:4;
(ff) Val (23)---Pro (79) of SEQ ID NO:4;
(gg) Val (23)---Asp (78) of SEQ ID NO:4;
(hh) Val (23)---Val (77) of SEQ ID NO:4;
(ii) Val (23)---Cys (76) of SEQ ID NO:4;
(jj) Leu (24)-Ile (108) of SEQ ID NO:4;
(kk) Glu (25)- Lys (107) of SEQ ID NO:4;
(ll) Val (26)---Arg (106) of SEQ ID NO:4;
(mm) Tyr (27)---Lys (105) of SEQ ID NO:4;
(nn) Tyr (28)---Phe (104) of SEQ ID NO:4;
(oo) Thr (29)---Val (103) of SEQ ID NO:4;
(pp) Ser (30)---Lys (107) of SEQ ID NO:4;
(qq) Ser (30)---Iys (105) of SEQ ID NO:4;
(rr) Ser (30)---Lys (93) of SEQ ID NO:4; and
(ss) Ser (30)---Cys (76) of SEQ ID NO:4.

9. The isolated polypeptide of claim 8, which is produced by a recombinant cell.

10. The isolated polypeptide of claim 9, wherein said recombinant cell is *E. coli.*

11. The isolated polypeptide of claim 9, wherein said recombinant cell is a COS cell.

12. The isolated polypeptide of claim 9, which is produced recombinantly using a baculovirus system.

13. The isolated polypeptide of claim 8, fused to a heterologous polypeptide.

14. A composition comprising the isolated polypeptide of claim 8 and a pharmaceutically acceptable carrier.

* * * * *